United States Patent
McElveen

(10) Patent No.: US 12,244,574 B2
(45) Date of Patent: *Mar. 4, 2025

(54) ENCODING / DECODING SYSTEM AND METHOD

(71) Applicant: LOGNOVATIONS HOLDINGS, LLC, Tampa, FL (US)

(72) Inventor: Christopher A. McElveen, Tampa, FL (US)

(73) Assignee: LogNovations Holdings, LLC, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/045,222

(22) Filed: Oct. 10, 2022

(65) Prior Publication Data

US 2023/0132017 A1 Apr. 27, 2023

Related U.S. Application Data

(60) Provisional application No. 63/272,539, filed on Oct. 27, 2021, provisional application No. 63/256,267, filed on Oct. 15, 2021.

(51) Int. Cl.
*H04L 9/40* (2022.01)
*G06F 16/11* (2019.01)
(Continued)

(52) U.S. Cl.
CPC ........ *H04L 63/0428* (2013.01); *G06F 16/116* (2019.01); *G06F 16/13* (2019.01);
(Continued)

(58) Field of Classification Search
CPC .................................................. H04L 63/0428
(Continued)

(56) References Cited

U.S. PATENT DOCUMENTS 5,838,963 A 11/1998 Griffiths
5,956,724 A 9/1999 Griffiths
(Continued)

FOREIGN PATENT DOCUMENTS

WO 99/14889 A1 3/1999
WO 2018/102861 A1 6/2018
(Continued)

OTHER PUBLICATIONS

Non-Final Office Action issued in related U.S. Appl. No. 18/045,213 on Mar. 31, 2023.
(Continued)

*Primary Examiner* — Muluemebet Gurmu
(74) *Attorney, Agent, or Firm* — McAndrews, Held & Malloy, Ltd.

(57) ABSTRACT

A computer-implemented method, computer program product and computing system for: processing an unencoded data file to identify a plurality of file segments; mapping each of the plurality of file segments to a portion of a dictionary file to generate a plurality of mappings, wherein each of the plurality of mappings includes a starting location and a length, thus generating a related encoded data file based, at least in part, upon the plurality of mappings; and storing the related encoded data file on a cloud-based storage platform.

24 Claims, 19 Drawing Sheets

(51) Int. Cl.

| | | |
|---|---|---|
| G06F 16/13 | (2019.01) | |
| G06F 16/174 | (2019.01) | |
| G06F 21/60 | (2013.01) | |
| G06F 21/62 | (2013.01) | |
| G16H 10/60 | (2018.01) | |
| H03M 7/30 | (2006.01) | |
| H04L 1/00 | (2006.01) | |
| H04L 9/00 | (2022.01) | |
| H04L 67/06 | (2022.01) | |
| H04W 4/80 | (2018.01) | |

(52) U.S. Cl.
CPC ........ *G06F 16/1744* (2019.01); *G06F 21/602* (2013.01); *G06F 21/6245* (2013.01); *G16H 10/60* (2018.01); *H03M 7/3066* (2013.01); *H03M 7/6011* (2013.01); *H04L 1/0056* (2013.01); *H04L 1/0064* (2013.01); *H04L 9/008* (2013.01); *H04L 67/06* (2013.01); *H04W 4/80* (2018.02); *H03M 7/3088* (2013.01); *H04L 2209/30* (2013.01)

(58) Field of Classification Search
USPC ......................................................... 707/693
See application file for complete search history.

(56) References Cited

U.S. PATENT DOCUMENTS

| | | |
|---|---|---|
| 6,272,658 B1 | 8/2001 | Steele et al. |
| 6,389,427 B1 | 5/2002 | Faulkner |
| 6,597,812 B1 | 7/2003 | Fallon et al. |
| 7,102,552 B1 | 9/2006 | Archbold et al. |
| 7,756,817 B2 | 7/2010 | Merchia et al. |
| 7,814,316 B1 | 10/2010 | Hughes et al. |
| 9,094,378 B1 | 7/2015 | Yung et al. |
| 2007/0008191 A1 | 1/2007 | Archbold et al. |
| 2007/0116055 A1 | 5/2007 | Atsumi et al. |
| 2007/0204057 A1 | 8/2007 | Shaver et al. |
| 2008/0204284 A1 | 8/2008 | Archbold et al. |
| 2008/0294909 A1 | 11/2008 | Ostrovsky et al. |
| 2010/0122312 A1 | 5/2010 | Green et al. |
| 2011/0191588 A1 | 8/2011 | Rogaway |
| 2012/0030375 A1 | 2/2012 | Schulenburg |
| 2012/0194361 A1* | 8/2012 | Archbold ............... H03M 7/30 341/87 |
| 2013/0036101 A1 | 2/2013 | Marwah et al. |
| 2013/0067237 A1 | 3/2013 | Huang et al. |
| 2013/0275391 A1 | 10/2013 | Batwara et al. |
| 2014/0095768 A1 | 4/2014 | Kipnis et al. |
| 2014/0304505 A1 | 10/2014 | Dawson |
| 2014/0372470 A1 | 12/2014 | Attaluri et al. |
| 2015/0025909 A1 | 1/2015 | Hayter, II |
| 2015/0039320 A1 | 2/2015 | Neuhauser et al. |
| 2015/0244517 A1* | 8/2015 | Nita .................... H04L 63/0428 713/168 |
| 2016/0105402 A1 | 4/2016 | Soon-Shiong et al. |
| 2017/0026656 A1 | 1/2017 | Aerts et al. |
| 2017/0212909 A1 | 7/2017 | Bakashi et al. |
| 2017/0286221 A1 | 10/2017 | Azogui et al. |
| 2017/0364450 A1 | 12/2017 | Struttmann |
| 2017/0374490 A1 | 12/2017 | Schoppmeier |
| 2018/0069696 A1 | 3/2018 | Yoo et al. |
| 2018/0212750 A1 | 7/2018 | Hoffstein et al. |
| 2018/0349740 A1 | 12/2018 | Schneider et al. |
| 2019/0058580 A1 | 2/2019 | Tormasov et al. |
| 2019/0065517 A1 | 2/2019 | Comertoglu et al. |
| 2019/0129640 A1 | 5/2019 | Riahi et al. |
| 2019/0138927 A1* | 5/2019 | Jeffries ................. H03M 7/70 |
| 2020/0110767 A1* | 4/2020 | Alakuijala ............ H03M 13/15 |
| 2020/0175178 A1 | 6/2020 | Li et al. |
| 2020/0228308 A1 | 7/2020 | Shainski et al. |
| 2020/0349741 A1 | 11/2020 | Hinnerson et al. |
| 2021/0073221 A1 | 3/2021 | Chavan et al. |
| 2021/0375008 A1 | 12/2021 | Hassan et al. |
| 2022/0191034 A1 | 6/2022 | Adams et al. |
| 2022/0405461 A1 | 12/2022 | Lempel et al. |
| 2023/0122581 A1 | 4/2023 | McElveen |

FOREIGN PATENT DOCUMENTS

| | | |
|---|---|---|
| WO | 2020/110830 A1 | 6/2020 |
| WO | 2023/064804 A1 | 4/2023 |
| WO | 2023/064842 A1 | 4/2023 |
| WO | 2023/064844 A1 | 4/2023 |
| WO | 2023/064846 A1 | 4/2023 |
| WO | 2023/064848 A1 | 4/2023 |
| WO | 2023/064852 A1 | 4/2023 |
| WO | 2023/064855 A1 | 4/2023 |
| WO | 2023/064862 A1 | 4/2023 |
| WO | 2023/064865 A1 | 4/2023 |

OTHER PUBLICATIONS

International Search Report and Written Opinion issued in related Application Serial No. PCT/US2022/077961 on Jan. 17, 2023.
International Search Report and Written Opinion issued in related Application Serial No. PCT/US2022/077965 on Jan. 17, 2023.
International Search Report and Written Opinion issued in related Application Serial No. PCT/US2022/077989 on Jan. 17, 2023.
International Search Report and Written Opinion issued in related Application Serial No. PCT/US2022/077993 on Jan. 17, 2023.
International Search Report and Written Opinion issued in related Application Serial No. PCT/US2022/077995 on Jan. 17, 2023.
International Search Report and Written Opinion issued in related Application Serial No. PCT/US2022/077996 on Jan. 17, 2023.
International Search Report and Written Opinion issued in related Application Serial No. PCT/US2022/077997 on Jan. 17, 2023.
International Search Report and Written Opinion issued in related Application Serial No. PCT/US2022/077998 on Jan. 17, 2023.
International Search Report and Written Opinion issued in related Application Serial No. PCT/US2022/078026 on Jan. 17, 2023.
International Search Report and Written Opinion issued in related Application Serial No. PCT/US2022/078032 on Jan. 17, 2023.
International Search Report and Written Opinion issued in related Application Serial No. PCT/US2022/078039 on Jan. 17, 2023.
International Search Report and Written Opinion issued in related Application Serial No. PCT/US2022/078044 on Jan. 17, 2023.
International Search Report and Written Opinion issued in related Application Serial No. PCT/US2022/078055 on Jan. 17, 2023.
International Search Report and Written Opinion issued in related Application Serial No. PCT/US2022/078058 on Jan. 17, 2023.
Naoki Katoh et al., "Sublinear Computation Paradigm, Algorithmic Revolution in the Big Data Era." Published by the registered company Springer Nature Singapore Pte Ltd. 2022. https://doi.org/10.1007/978-981-16-4095-7. pp. 1-410.
Final Office Action issued in related U.S. Appl. No. 17/938,836 on issue Date; Apr. 19, 2024.
Non-Final Office Action issued in related U.S. Appl. No. 18/045,220 on issue Date; Mar. 26, 2024.
Notice of Allowance issued in related U.S. Appl. No. 18/045,224 on issue Dater; Mar. 27, 2024.
Notice of Allowance issued in related U.S. Appl. No. 18/045,246 on issue Date; Mar. 15, 2024.
Notice of Allowance issued in related U.S. Appl. No. 18/045,246 on issue Date; Mar. 27, 2024.
Non-Final Office Action issued in related U.S. Appl. No. 18/045,224 on Oct. 13, 2023.
Final Office Action issued in related U.S. Appl. No. 18/045,213 on Nov. 1, 2023.
Non-Final Office Action issued in related U.S. Appl. No. 18/045,246 on Oct. 24, 2023.
Non-Final Office Action issued in related U.S. Appl. No. 17/938,819 on Jun. 25, 2024.
Non-Final Office Action issued in related U.S. Appl. No. 17/938,847 on Jun. 21, 2024.
Non-Final Office Action issued in related U.S. Appl. No. 18/045,213 on issue Date; Apr. 24, 2024.

(56) References Cited

OTHER PUBLICATIONS

Notice of Allowance issued in related U.S. Appl. No. 18/045,224 on issue Date May 14, 2024.
Notice of Allowance issued in related U.S. Appl. No. 18/045,246 on issue Date: May 14, 2024.
Notice of Allowance issued in related U.S. Appl. No. 18/045,246 on Jun. 21, 2024.
Non-Final Office Action issued in related U.S. Appl. No. 17/938,836 on Nov. 9, 2023.
Coveroth, EL15: What is Homomorphic Encryption, https://www.reddit.com/r/explainlikeimfive/comments/5qea0u/eli5_what_is_homomorphic_encryption, Jan. 27, 2017 (Year: 2017).
International Search Report and Written Opinion issued in related Application Serial No. PCT/US2022/077991 on Jan. 10, 2023.
International Search Report and Written Opinion issued in related Application Serial No. PCT/US2022/078022 on Jan. 10, 2023.
International Search Report and Written Opinion issued in related Application Serial No. PCT/US2022/078024 on Jan. 10, 2023.
Non-Final Office Action issued in related U.S. Appl. No. 17/938,849 on issue Date; Feb. 15, 2024.
Non-Final Office Action issued in related U.S. Appl. No. 17/938,862 on Sep. 3, 2024.
Non-Final Office Action issued in related U.S. Appl. No. 17/938,900 on Sep. 4, 2024.
Non-Final Office Action issued in related U.S. Appl. No. 18/045,230 on Jul. 2, 2024.
Non-Final Office Action issued in related U.S. Appl. No. 18/045,248 on Jul. 19, 2024.
Notice of Allowance issued in related U.S. Appl. No. 17/938,836 on Aug. 8, 2024.
Notice of Allowance issued in related U.S. Appl. No. 17/938,883 on Sep. 30, 2024.
Notice of Allowance issued in related U.S. Appl. No. 18/045,224 on Aug. 5, 2024.
Notice of Allowance issued in related U.S. Appl. No. 18/045,224 on issue Aug. 23, 2024.
Notice of Allowance issued in related U.S. Appl. No. 18/045,224 on Sep. 26, 2024.

* cited by examiner

ENCODING / DECODING SYSTEM AND METHOD

RELATED APPLICATION(S)

This application claims the benefit of U.S. Provisional Application No(s).: 63/256,267 filed on 15 Oct. 2021, and 63/272,539 filed on 27 Oct. 2021, the entire contents of which are incorporated herein by reference.

TECHNICAL FIELD

This disclosure relates to data encoding and, more particularly, to systems and methods that allow for the processing of encoded data without the need for decoding.

BACKGROUND

Data may be encoded and decoded to transform the data from a first form to a second form to achieve a certain task. One example of such encoding may be data compression, wherein data is transformed from a first form (e.g., a larger form) to a second form (e.g., a smaller form) to achieve the task of saving storage space. Another example of such encoding may be data encryption, wherein data is transformed from a first form (e.g., an unencrypted form) to a second form (e.g., an encrypted form) to achieve the task of securing the data.

Unfortunately and when using such encoded data (e.g., accessing the data, manipulating the data), the encoded data would first need to be decoded (e.g., decompressed/decrypted), then used (e.g., accessed/manipulated), and then reencoded (compressed/encrypted). As could be imagined, such decoding and subsequent reencoding is expensive from a computational and availability point of view.

SUMMARY OF DISCLOSURE

Encoded Data (at Rest Cloud-Based Storage)

In one implementation, a computer-implemented method is executed on a computing device and includes: processing an unencoded data file to identify a plurality of file segments; mapping each of the plurality of file segments to a portion of a dictionary file to generate a plurality of mappings, wherein each of the plurality of mappings includes a starting location and a length, thus generating a related encoded data file based, at least in part, upon the plurality of mappings; and storing the related encoded data file on a cloud-based storage platform.

One or more of the following features may be included. A request to manipulate the unencoded data file may be received. The related encoded data file may be processed based, at least in part, upon the plurality of mappings and the dictionary file to generate a modified encoded data file that represents the requested manipulations of the unencoded data file. Processing the related encoded data file based, at least in part, upon the plurality of mappings and the dictionary file to generate a modified encoded data file that represents the requested manipulations of the unencoded data file may include one or more of: performing a homomorphic encoding operation; and performing a heteromorphic encoding operation. The related encoded data file may include one or more of: a related compressed data file; and a related encrypted data file. The dictionary file may include a plurality of discrete entries. Processing the related encoded data file based, at least in part, upon the plurality of mappings and the dictionary file to generate a modified encoded data file that represents the requested manipulations of the unencoded data file may include: processing the related encoded data file, in a byte-wise fashion, based upon the plurality of mappings and the dictionary file to generate a modified encoded data file that represents the requested manipulations of the unencoded data file. The dictionary file may include a plurality of concatenated entries. Processing the related encoded data file based, at least in part, upon the plurality of mappings and the dictionary file to generate a modified encoded data file that represents the requested manipulations of the unencoded data file may include: processing the related encoded data file, in a bit-wise fashion, based upon the plurality of mappings and the dictionary file to generate a modified encoded data file that represents the requested manipulations of the unencoded data file. The related encoded data file may be generated on the cloud-based storage platform. The related encoded data file may be generated outside of the cloud-based storage platform.

In another implementation, a computer program product resides on a computer readable medium and has a plurality of instructions stored on it. When executed by a processor, the instructions cause the processor to perform operations including: processing an unencoded data file to identify a plurality of file segments; mapping each of the plurality of file segments to a portion of a dictionary file to generate a plurality of mappings, wherein each of the plurality of mappings includes a starting location and a length, thus generating a related encoded data file based, at least in part, upon the plurality of mappings; and storing the related encoded data file on a cloud-based storage platform.

One or more of the following features may be included. A request to manipulate the unencoded data file may be received. The related encoded data file may be processed based, at least in part, upon the plurality of mappings and the dictionary file to generate a modified encoded data file that represents the requested manipulations of the unencoded data file. Processing the related encoded data file based, at least in part, upon the plurality of mappings and the dictionary file to generate a modified encoded data file that represents the requested manipulations of the unencoded data file may include one or more of: performing a homomorphic encoding operation; and performing a heteromorphic encoding operation. The related encoded data file may include one or more of: a related compressed data file; and a related encrypted data file. The dictionary file may include a plurality of discrete entries. Processing the related encoded data file based, at least in part, upon the plurality of mappings and the dictionary file to generate a modified encoded data file that represents the requested manipulations of the unencoded data file may include: processing the related encoded data file, in a byte-wise fashion, based upon the plurality of mappings and the dictionary file to generate a modified encoded data file that represents the requested manipulations of the unencoded data file. The dictionary file may include a plurality of concatenated entries. Processing the related encoded data file based, at least in part, upon the plurality of mappings and the dictionary file to generate a modified encoded data file that represents the requested manipulations of the unencoded data file may include: processing the related encoded data file, in a bit-wise fashion, based upon the plurality of mappings and the dictionary file to generate a modified encoded data file that represents the requested manipulations of the unencoded data file. The related encoded data file may be generated on the cloud-based storage platform. The related encoded data file may be generated outside of the cloud-based storage platform.

In another implementation, a computing system includes a processor and memory is configured to perform operations including: processing an unencoded data file to identify a plurality of file segments; mapping each of the plurality of file segments to a portion of a dictionary file to generate a plurality of mappings, wherein each of the plurality of mappings includes a starting location and a length, thus generating a related encoded data file based, at least in part, upon the plurality of mappings; and storing the related encoded data file on a cloud-based storage platform.

One or more of the following features may be included. A request to manipulate the unencoded data file may be received. The related encoded data file may be processed based, at least in part, upon the plurality of mappings and the dictionary file to generate a modified encoded data file that represents the requested manipulations of the unencoded data file. Processing the related encoded data file based, at least in part, upon the plurality of mappings and the dictionary file to generate a modified encoded data file that represents the requested manipulations of the unencoded data file may include one or more of: performing a homomorphic encoding operation; and performing a heteromorphic encoding operation. The related encoded data file may include one or more of: a related compressed data file; and a related encrypted data file. The dictionary file may include a plurality of discrete entries. Processing the related encoded data file based, at least in part, upon the plurality of mappings and the dictionary file to generate a modified encoded data file that represents the requested manipulations of the unencoded data file may include: processing the related encoded data file, in a byte-wise fashion, based upon the plurality of mappings and the dictionary file to generate a modified encoded data file that represents the requested manipulations of the unencoded data file. The dictionary file may include a plurality of concatenated entries. Processing the related encoded data file based, at least in part, upon the plurality of mappings and the dictionary file to generate a modified encoded data file that represents the requested manipulations of the unencoded data file may include: processing the related encoded data file, in a bit-wise fashion, based upon the plurality of mappings and the dictionary file to generate a modified encoded data file that represents the requested manipulations of the unencoded data file. The related encoded data file may be generated on the cloud-based storage platform. The related encoded data file may be generated outside of the cloud-based storage platform.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
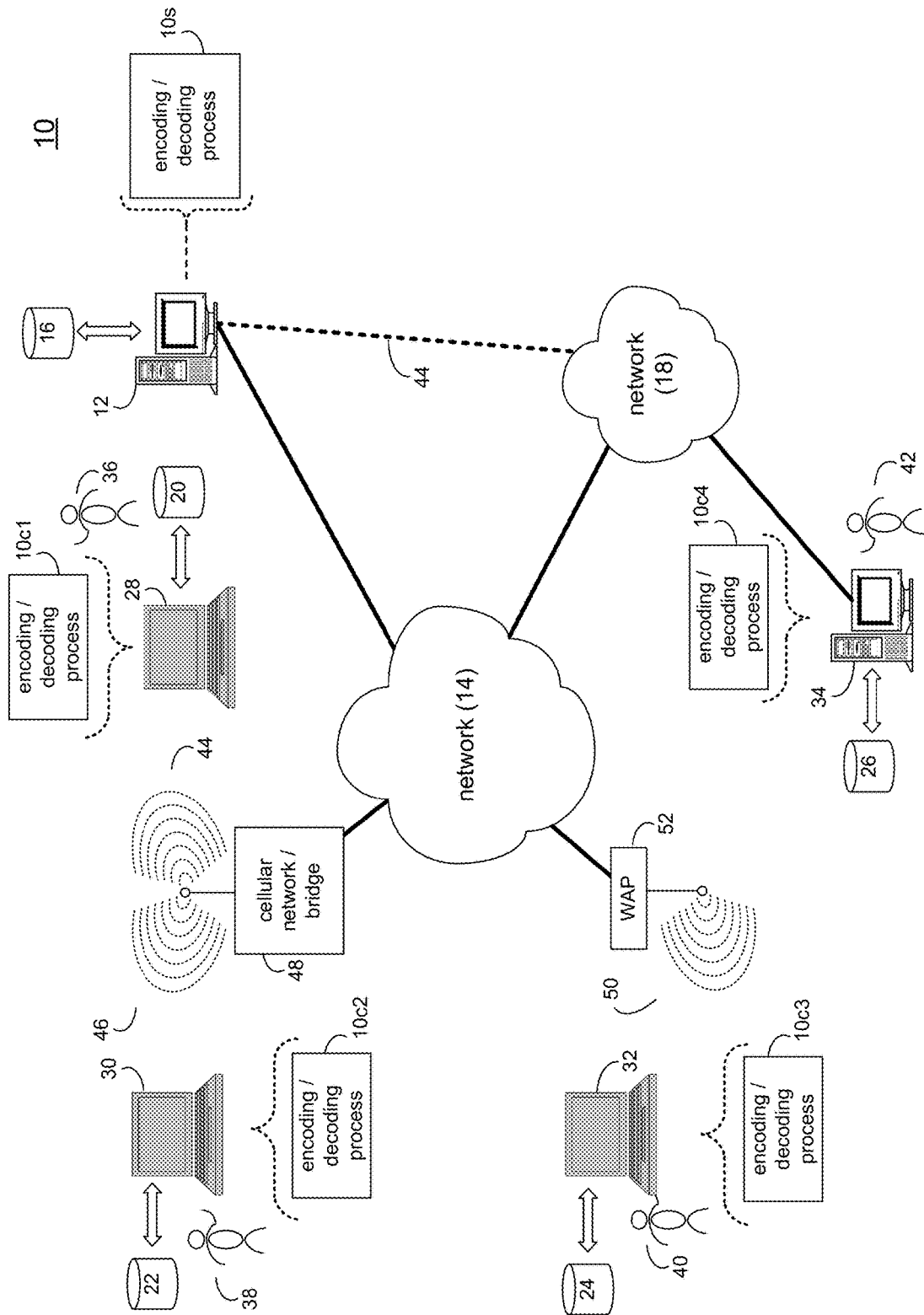
FIG. 1 is a diagrammatic view of a distributed computing network including a computing device that executes an encoding/decoding process according to an embodiment of the present disclosure.

Referring to FIG. 1, there is shown encoding/decoding process 10. Encoding/decoding process 10 may be implemented as a server-side process, a client-side process, or a hybrid server-side/client-side process. For example, encoding/decoding process 10 may be implemented as a purely server-side process via encoding/decoding process 10s. Alternatively, encoding/decoding process 10 may be implemented as a purely client-side process via one or more of encoding/decoding process 10c1, encoding/decoding process 10c2, encoding/decoding process 10c3, and encoding/decoding process 10c4. Alternatively still, encoding/decoding process 10 may be implemented as a hybrid server-side/client-side process via encoding/decoding process 10s in combination with one or more of encoding/decoding process 10c1, encoding/decoding process 10c2, encoding/decoding process 10c3, and encoding/decoding process 10c4. Accordingly, encoding/decoding process 10 as used in this disclosure may include any combination of encoding/decoding process 10s, encoding/decoding process 10c1, encoding/decoding process 10c2, encoding/decoding process 10c3, and encoding/decoding process 10c4.

Encoding/decoding process 10s may be a server application and may reside on and may be executed by computing device 12, which may be connected to network 14 (e.g., the Internet or a local area network). Examples of computing device 12 may include, but are not limited to: a personal computer, a server computer, a series of server computers, a mini computer, a mainframe computer, a smartphone, or a cloud-based computing platform.

The instruction sets and subroutines of encoding/decoding process 10s, which may be stored on storage device 16 coupled to computing device 12, may be executed by one or more processors (not shown) and one or more memory architectures (not shown) included within computing device 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Examples of encoding/decoding processes 10c1, 10c2, 10c3, 10c4 may include but are not limited to a web browser, a game console user interface, a mobile device user interface, or a specialized application (e.g., an application running on e.g., the Android™ platform, the iOS™ platform, the Windows™ platform, the Linux™ platform or the UNIX™ platform). The instruction sets and subroutines of encoding/decoding processes 10c1, 10c2, 10c3, 10c4, which may be stored on storage devices 20, 22, 24, 26 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Examples of storage devices 20, 22, 24, 26 may include but are not limited to: hard disk drives; RAID devices; random access memories (RAM); read-only memories (ROM), and all forms of flash memory storage devices.

Examples of client electronic devices 28, 30, 32, 34 may include, but are not limited to, a smartphone (not shown), a personal digital assistant (not shown), a tablet computer (not shown), laptop computers 28, 30, 32, personal computer 34, a notebook computer (not shown), a server computer (not shown), a gaming console (not shown), and a dedicated network device (not shown). Client electronic devices 28, 30, 32, 34 may each execute an operating system, examples of which may include but are not limited to Microsoft Windows™, Android™, iOS™, Linux™, or a custom operating system.

Users 36, 38, 40, 42 may access encoding/decoding process 10 directly through network 14 or through secondary network 18. Further, encoding/decoding process 10 may be connected to network 14 through secondary network 18, as illustrated with link line 44.

The various client electronic devices (e.g., client electronic devices 28, 30, 32, 34) may be directly or indirectly coupled to network 14 (or network 18). For example, laptop computer 28 and laptop computer 30 are shown wirelessly coupled to network 14 via wireless communication channels 44, 46 (respectively) established between laptop computers 28, 30 (respectively) and cellular network/bridge 48, which is shown directly coupled to network 14. Further, laptop computer 32 is shown wirelessly coupled to network 14 via wireless communication channel 50 established between laptop computer 32 and wireless access point (i.e., WAP) 52, which is shown directly coupled to network 14. Additionally, personal computer 34 is shown directly coupled to network 18 via a hardwired network connection.

WAP 52 may be, for example, an IEEE 802.11a, 802.11b, 802.11g, 802.11n, Wi-Fi, and/or Bluetooth device that is capable of establishing wireless communication channel 50 between laptop computer 32 and WAP 52. As is known in the art, IEEE 802.11x specifications may use Ethernet protocol and carrier sense multiple access with collision avoidance (i.e., CSMA/CA) for path sharing. As is known in the art, Bluetooth is a telecommunications industry specification that allows e.g., mobile phones, computers, and personal digital assistants to be interconnected using a short-range wireless connection.

Encoding/Decoding Process

Figure 2:
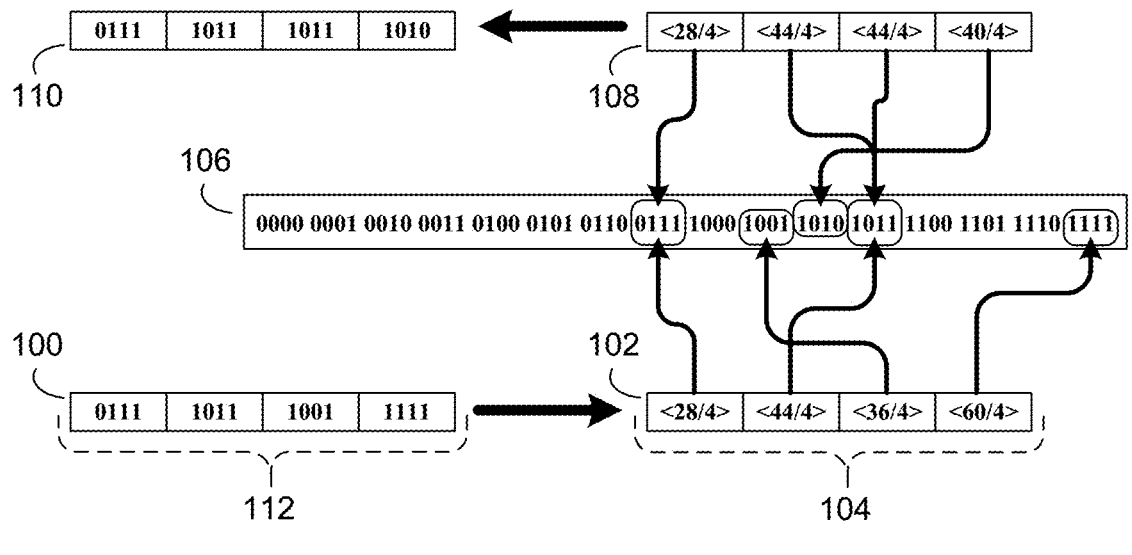
FIG. 2 is a diagrammatic view of various pieces of content accessible by the encoding/decoding process of FIG. 1 according to an embodiment of the present disclosure.
Figure 2:
Figure 2:
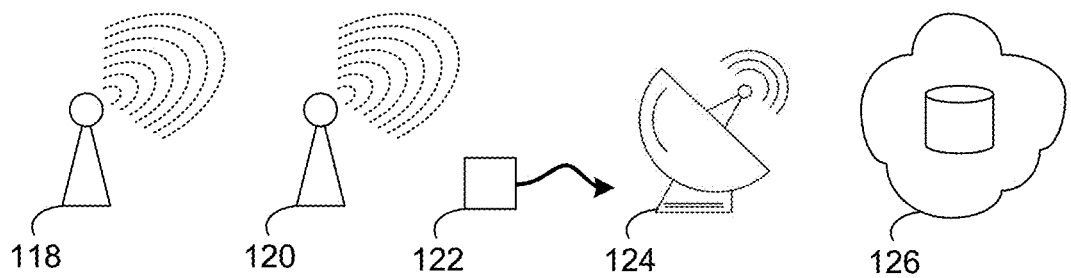
Figure 2:
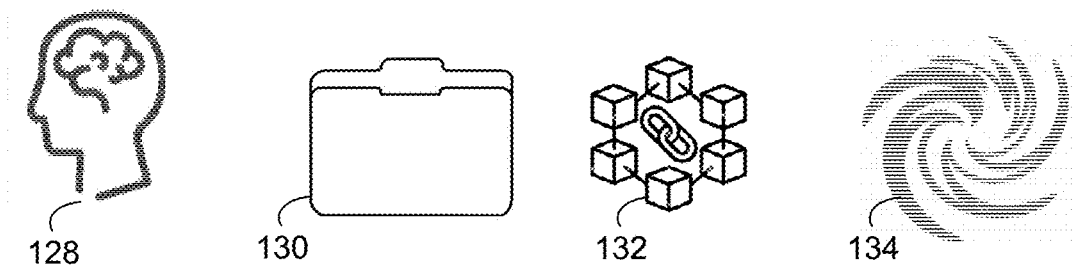

Referring also to FIG. 2 and as will be discussed below in greater detail, encoding/decoding process 10 may be configured to allow for the encoding and subsequent decoding of data (e.g., first data file 100). Examples of such encoding/decoding may include but are not limited to: compression/decompression and encryption/decryption. Further and as will be discussed below in greater detail, encoding/decoding process 10 may be configured to allow for the manipulation of such encoded data (e.g., compressed data and/or encrypted data) without the need to first decode (e.g., decompress and/or decrypt) the encoded data.

Compression/Decompression: As is known in the art, data compression (or source coding or bit-rate reduction) is the process of encoding information using fewer bits than the original representation. Any particular compression is either lossy or lossless. Lossless compression reduces bits by identifying and eliminating statistical redundancy. No information is lost in lossless compression. Lossy compression reduces bits by removing unnecessary or less important information. Typically, a device that performs data compression is referred to as an encoder, and one that performs the reversal of the process (decompression) as a decoder. The process of reducing the size of a data file is often referred to as data compression. In the context of data transmission, it is called source coding; encoding done at the source of the data before it is stored or transmitted. Compression is useful because it reduces the resources required to store and transmit data. Computational resources are consumed in the compression and decompression processes. Data compression is subject to a space-time complexity trade-off. For instance, a compression scheme for video may require expensive hardware for the video to be decompressed fast enough to be viewed as it is being decompressed, and the option to decompress the video in full before watching it may be inconvenient or require additional storage. The design of data compression schemes involves trade-offs among various factors, including the degree of compression, the amount of distortion introduced (when using lossy data compression), and the computational resources required to compress and decompress the data.

Encryption/Decryption: As is known in the art, data encryption is the process of encoding information, wherein the process converts the original representation of the information (known as plaintext), into an alternative form (known as ciphertext). Ideally, only authorized parties can decipher a ciphertext back to plaintext and access the original information. Encryption does not itself prevent interference but denies the intelligible content to a would-be interceptor. For technical reasons, an encryption scheme usually uses a pseudo-random encryption key generated by an algorithm. It is possible to decrypt the message without possessing the key but, for a well-designed encryption scheme, considerable computational resources and skills are required. An authorized recipient can easily decrypt the message with the key provided by the originator to recipients but not to unauthorized users. Historically, various forms of encryption have been used to aid in cryptography. Early encryption techniques were often used in military messaging. Since then, new techniques have emerged and become commonplace in all areas of modern computing. Modern encryption schemes use the concepts of public-key and symmetric-key and may ensure security because modern computers are inefficient at cracking the encryption.

System Overview

The following discussion concerns a system overview of encoding/decoding process 10.

Figure 3:
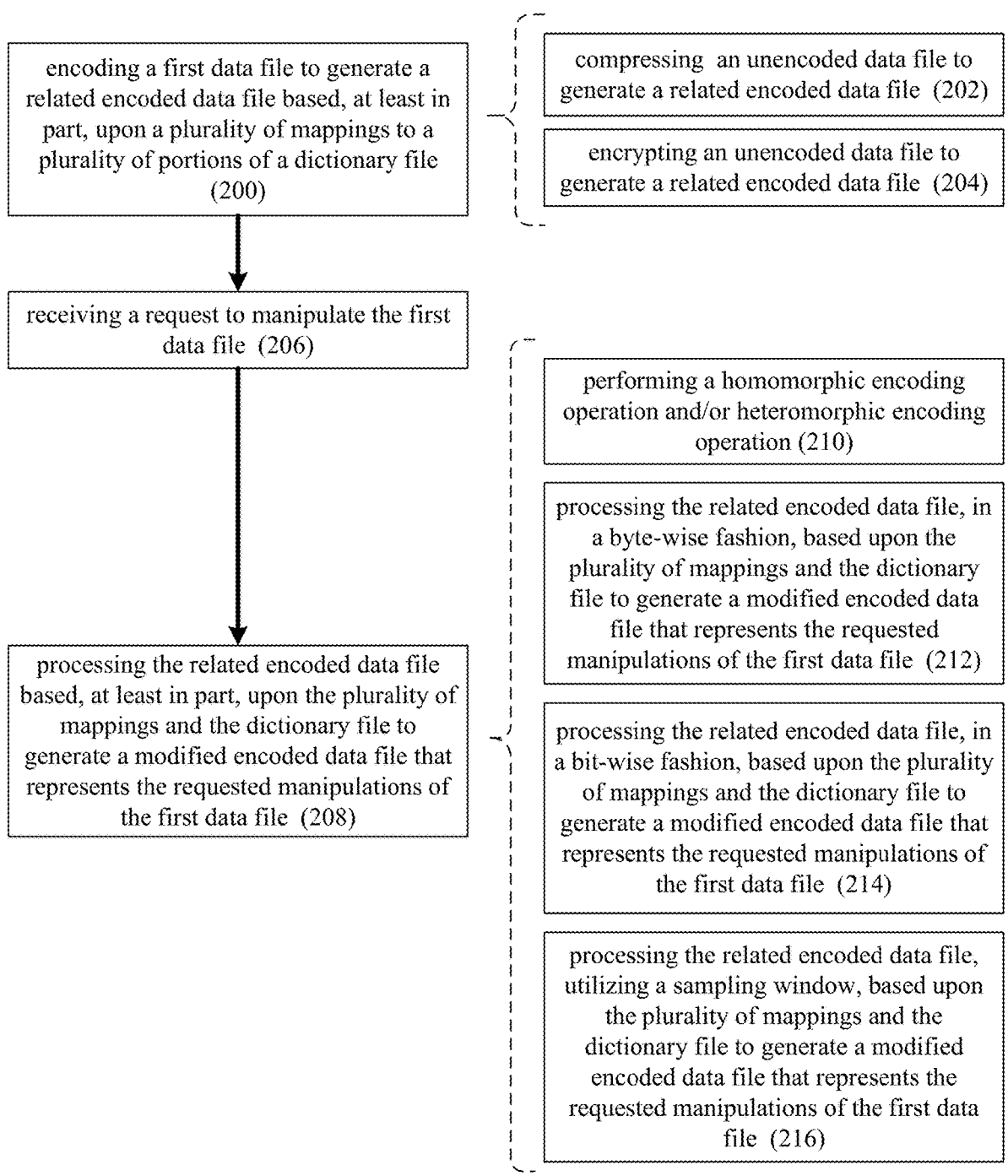
FIG. 3 is a flowchart of the encoding/decoding process of FIG. 1 according to an embodiment of the present disclosure.

Referring also to FIG. 3, encoding/decoding process 10 may encode 200 a first data file (e.g., first data file 100) to generate a related encoded data file (e.g., related encoded data file 102) based, at least in part, upon a plurality of mappings (e.g., plurality of mappings 104) to a plurality of portions of a dictionary file (e.g., dictionary file 106).

This first data file (e.g., first data file 100) may essentially be any type of data file, examples of which may include but are not limited to: a first compressed data file; a first uncompressed data file; a first encrypted data file; a first unencrypted data file; a first encoded data file; and a first unencoded data file.

As will be discussed below in greater detail, each of the plurality of mappings (e.g., plurality of mappings 104) may include a starting location and a length that points to a particular portion of the dictionary file (e.g., dictionary file 106). One example of such mappings may include but is not limited to <IJ> pairs, wherein the "I" is indicative of the starting location (within dictionary file 106) and the "J" is indicative of the length of the data being pointed to. As will be discussed below in greater detail, the dictionary file (e.g., dictionary file 106) may include a plurality of discrete entries or a plurality of concatenated entries.

Generally speaking, the dictionary file (e.g., dictionary file 106) may function as a cipher that effectuates the encoding/decoding of first data file 100. In one non-limiting example, the dictionary file (e.g., dictionary file 106) may include all of the possible combinations of a number that have a defined bit length, wherein this defined bit length may vary depending upon the design criteria of encoding/decoding process 10.

For illustrative purposes only, assume that dictionary file 106 includes entries having a defined bit length of four bits. As is known in the art, a four-bit entry has $2^4$ possible values, namely:

0000 (binarily representing a decimal value of 0)
0001 (binarily representing a decimal value of 1)
0010 (binarily representing a decimal value of 2)
0011 (binarily representing a decimal value of 3)
0100 (binarily representing a decimal value of 4)
0101 (binarily representing a decimal value of 5)
0110 (binarily representing a decimal value of 6)
0111 (binarily representing a decimal value of 7)
1000 (binarily representing a decimal value of 8)
1001 (binarily representing a decimal value of 9)
1010 (binarily representing a decimal value of 10)
1011 (binarily representing a decimal value of 11)
1100 (binarily representing a decimal value of 12)
1101 (binarily representing a decimal value of 13)
1110 (binarily representing a decimal value of 14)
1111 (binarily representing a decimal value of 15)

Accordingly, dictionary file 106 may include entries that define each of the above-described sixteen possible values. While the above-described example concerns a dictionary file 106 including entries having a defined bit length of four bits, this is for illustrative purposes only and is not intended to be a limitation of this disclosure, as other configurations are possible and are considered to be within the scope of this disclosure. Further, it is likely that the entries defined within dictionary file 106 may have a defined bit length greater than four bits (e.g., 8 bits, 16 bits, 32 bits, 64 bits).

As stated above, the dictionary file (e.g., dictionary file 106) may include a plurality of discrete entries or a plurality of concatenated entries.

When the dictionary file (e.g., dictionary file 106) includes a plurality of discrete entries, dictionary file 106 may be configured as follows:

0000 0001 0010 0011 0100 0101 0110 0111 1000 1001 1010 1011 1100 1101 1110 1111 wherein each entry within the dictionary file (e.g., dictionary file 106) is separated (e.g., by a black space, a comma, or a slash), thus resulting in (in this example) sixteen discrete entries.

When the dictionary file (e.g., dictionary file 106) includes a plurality of concatenated entries, dictionary file 106 may be configured as follows:

0000000100100011010001010110011110001001101010 111100110111101111 wherein each entry within the dictionary file (e.g., dictionary file 106) is not separated, thus resulting in (in this example) sixteen concatenated entries coupled end-to-end to form (in this example) a single sixty-four bit dictionary file.

As discussed above, each of the plurality of mappings (e.g., plurality of mappings 104) may include a starting location and a length that points to a particular portion of the dictionary file (e.g., dictionary file 106), wherein one such example of these mappings may include but is not limited to <IJ> pairs.

Assume that the first data file 100 to be encoded is:
0111 1011 1001 1111

Accordingly, when encoding/decoding process 10 encodes 200 first data file 100, the resulting encoded data file (e.g., related encoded data file 102) generated may include four mappings (e.g., plurality of mappings 104) that map to the appropriate portions of dictionary file 106. Specifically:

a first mapping <28/4> that defines an offset of 28 bits from the beginning of dictionary file 106 and a read length of 4 bits, thus mapping to 0111 within dictionary file 106;

a second mapping <44/4> that defines an offset of 44 bits from the beginning of dictionary file 106 and a read length of 4 bits, thus mapping to 1011 within dictionary file 106;

a third mapping <36/4> that defines an offset of 36 bits from the beginning of dictionary file 106 and a read length of 4 bits, thus mapping to 1001 within dictionary file 106; and a fourth mapping <60/4> that defines an offset of 60 bits from the beginning of dictionary file 106 and a read length of 4 bits, thus mapping to 1111 within dictionary file 106.

Accordingly and in the above stated example, when encoding/decoding process 10 encodes 200 first data file 100 (e.g., 0111 1011 1001 1111), the resulting encoded data file (e.g., related encoded data file 102) generated may include four mappings (e.g., <28/4> <44/4> <36/4> <60/4>). Accordingly and through the use of these four mappings (i.e., related encoded data file 102), first data file 100 may be decoded by using this plurality of mappings (.e., plurality of mappings 104) to regenerate first data file 100. Specifically:

the first mapping <28/4> within related encoded data file 102 may be utilized by encoding/decoding process 10 to obtain from dictionary file 106 the data portion that is being pointed to by this mapping, namely the data portion 0111 within dictionary file 106;

the second mapping <44/4> within related encoded data file 102 may be utilized by encoding/decoding process 10 to obtain from dictionary file 106 the data portion that is being pointed to by this mapping, namely the data portion 1011 within dictionary file 106;

the third mapping <36/4> within related encoded data file 102 may be utilized by encoding/decoding process 10 to obtain from dictionary file 106 the data portion that is being pointed to by this mapping, namely the data portion 1001 within dictionary file 106; and the fourth mapping <60/4> within related encoded data file 102 may be utilized by encoding/decoding process 10 to obtain from dictionary file 106 the data portion that is being pointed to by this mapping, namely the data portion 1111 within dictionary file 106.

Accordingly and through the use of dictionary file 106 and plurality of mappings 104 included within related encoded data file 102, first data file 100 may be obtained.

When encoding 200 a first data file (e.g., first data file 100) to generate a related encoded data file (e.g., related encoded data file 102) based, at least in part, upon a plurality of mappings (e.g., plurality of mappings 104) to a plurality of portions of a dictionary file (e.g., dictionary file 106), encoding/decoding process 10 may: compress 202 an unencoded data file (e.g., first data file 100) to generate the related encoded data file (e.g., related encoded data file 102); and/or encrypt 204 an unencoded data file (e.g., first data file 100) to generate the related encoded data file (e.g., related encoded data file 102).

Encoding/decoding process 10 may receive 206 a request (e.g., request 160) to manipulate the first data file (e.g., first data file 100), wherein the requested manipulations may concern one or more of: a computation operation; a search operation; an append operation; a splitting operation; a joining operation; and a concatenating operation.

As is known in the art:

a computation operation may include but is not limited to a requested operation to mathematically manipulate the first data file (e.g., first data file 100);

a search operation may include but is not limited to a requested operation to search the first data file (e.g., first data file 100);

an append operation may include but is not limited to a requested operation to add to (i.e., append) the first data file (e.g., first data file 100);

a splitting operation may include but is not limited to a requested operation to divide (i.e., split) the first data file (e.g., first data file 100);

a joining operation may include but is not limited to a requested operation to join the first data file (e.g., first data file 100) with one or more other data files (not shown); and a concatenating operation may include but is not limited to a requested operation to combine the first data file (e.g., first data file 100) with another data file (not shown).

Encoding/decoding process 10 may then process 208 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the first data file (e.g., first data file 100).

As discussed above, encoding/decoding process 10 may be configured to allow for the manipulation of such encoded data (e.g., compressed data and/or encrypted data) without the need to first decode (e.g., decompress and/or decrypt) the encoded data (e.g., compressed data and/or encrypted data).

Continuing with the above stated example, assume that encoding/decoding process 10 encodes 200 first data file 100 (e.g., 0111 1011 1001 1111) into related encoded data file 102 (e.g., <28/4> <44/4> <36/4> <60/4>). Further, assume that encoding/decoding process 10 receives 206 a request (e.g., request 160) to add twenty-seven to first data file 100 (e.g., 0111 1011 1001 1111).

Accordingly and when processing 208 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the first data file (e.g., first data file 100), encoding/decoding process 10 may utilize the mappings within the related encoded data file (e.g., related encoded data file 102) to obtain the appropriate data portions within dictionary file 106. It is important to note that such a processing 208 operation does not require the manipulation/modification/decoding of the related encoded data file (e.g., related encoded data file 102); all that is required is that the mappings 104 within the related encoded data file 102 be read so that the related data portions can be obtained from the dictionary file (e.g., dictionary file 106).

Accordingly and when processing 208 the related encoded data file (e.g., related encoded data file 102):

the first mapping <28/4> within related encoded data file 102 may be utilized by encoding/decoding process 10 to obtain from dictionary file 106 the data portion that is being pointed to by this mapping, namely the data portion 0111 within dictionary file 106;

the second mapping <44/4> within related encoded data file 102 may be utilized by encoding/decoding process 10 to obtain from dictionary file 106 the data portion that is being pointed to by this mapping, namely the data portion 1011 within dictionary file 106;

the third mapping <36/4> within related encoded data file 102 may be utilized by encoding/decoding process 10 to obtain from dictionary file 106 the data portion that is being pointed to by this mapping, namely the data portion 1001 within dictionary file 106; and the fourth mapping <60/4> within related encoded data file 102 may be utilized by encoding/decoding process 10 to obtain from dictionary file 106 the data portion that is being pointed to by this mapping, namely the data portion 1111 within dictionary file 106.

Accordingly and through the use of dictionary file 106 and plurality of mappings 104 included within related encoded data file 102, first data file 100 (e.g., 0111 1011 1001 1111) may be obtained. Once obtained, encoding/decoding process 10 may perform the manipulation defined within the request (e.g., request 160) received 206.

In this particular illustrative example, the request (e.g., request 160) received 206 concerned adding twenty-seven to first data file 100 (e.g., 0111 1011 1001 1111). As is known in the art, the sixteen-bit representation of twenty-seven is 0000 0000 0001 1011. Accordingly and when processing 208 the related encoded data file (e.g., related encoded data file 102), encoding/decoding process 10 may add 0000 0000 0001 1011 to 0111 1011 1001 1111 (i.e., first data file 100) and get the result 0111 1011 1011 1010 (e.g., result 110).

When processing 208 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the first data file (e.g., first data file 100), encoding/decoding process 10 may: perform 210 a homomorphic encoding operation and/or a heteromorphic encoding operation on e.g., result 110.

As discussed above and when processing 208 the related encoded data file (e.g., related encoded data file 102), encoding/decoding process 10 may define result 110 (e.g., 0111 1011 1011 1010), wherein result 110 may be encoded via a homomorphic or heteromorphic encryption process. For example, if encoding/decoding process 10 encodes result 110 using the same encoding procedure that was used to encode first data file 100, this may be referred to as performing 210 a homomorphic encoding operation on result 110 (as both encoding operations are the same). Conversely, if encoding/decoding process 10 encodes result 110 using a different encoding procedure than that used to encode first data file 100, this may be referred to as performing 210 a heteromorphic encoding operation on result 110 (as the encoding operations are different).

Further and when processing 208 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the first data file (e.g., first data file 100), encoding/decoding process 10 may:

- process 212 the related encoded data file (e.g., related encoded data file 102), in a byte-wise fashion, based upon the plurality of mappings (e.g., plurality of mappings 104) and the dictionary file (e.g., dictionary file 106) to generate a modified encoded data file (e.g., modified encoded data file 108) that represents the requested manipulations of the first data file (e.g., first data file 100);
- process 214 the related encoded data file (e.g., related encoded data file 102), in a bit-wise fashion, based upon the plurality of mappings (e.g., plurality of mappings 104) and the dictionary file (e.g., dictionary file 106) to generate a modified encoded data file (e.g., modified encoded data file 108) that represents the requested manipulations of the first data file (e.g., first data file 100); and/or
- process 216 the related encoded data file (e.g., related encoded data file 102), utilizing a sampling window, based upon the plurality of mappings (e.g., plurality of mappings 104) and the dictionary file (e.g., dictionary file 106) to generate a modified encoded data file (e.g., modified encoded data file 108) that represents the requested manipulations of the first data file (e.g., first data file 100).

Assume that encoding/decoding process 10 encodes result 110 (e.g., 0111 1011 1011 1010) using the same encoding procedure that was used to encode first data file 100 (namely using dictionary file 106). Accordingly and when encoding result 110 (e.g., 0111 1011 1011 1010) to generate modified encoded data file 108, encoding/decoding process 10 may scan result 110 (e.g., 0111 1011 1011 1010) to define mappings that point to the various portions of result 110 (e.g., 0111 1011 1011 1010) within dictionary file 106.

As discussed above, the dictionary file (e.g., dictionary file 106) includes entries, that define each of the above-described sixteen possible values, namely:

0000 0001 0010 0011 0100 0101 0110 0111 1000 1001 1010 1011 1100 1101 1110 1111

Accordingly and when encoding/decoding process 10 scans result 110 (e.g., 0111 1011 1011 1010) to define mappings that point to the various portions of result 110 (e.g., 0111 1011 1011 1010) within dictionary file 106, encoding/decoding process 10 may define the following mappings for inclusion within modified encoded data file 108:

- a first mapping <28/4> that defines an offset of 28 bits from the beginning of dictionary file 106 and a read length of 4 bits, thus mapping to 0111 within dictionary file 106;
- a second mapping <44/4> that defines an offset of 44 bits from the beginning of dictionary file 106 and a read length of 4 bits, thus mapping to 1011 within dictionary file 106;
- a third mapping <44/4> that defines an offset of 36 bits from the beginning of dictionary file 106 and a read length of 4 bits, thus mapping to 1011 within dictionary file 106; and
- a fourth mapping <40/4> that defines an offset of 60 bits from the beginning of dictionary file 106 and a read length of 4 bits, thus mapping to 1010 within dictionary file 106.

Accordingly, encoding/decoding process 10 may utilize dictionary file 106 to encode result 110 (e.g., 0111 1011 1011 1010) into modified encoded data file 108 that includes the above-described plurality of mappings (e.g., <28/4> <44/4> <44/4> <40/4>).

As discussed above, encoding/decoding process 10 may scan result 110 (e.g., 0111 1011 1011 1010) to define mappings that point to the various portions of result 110 (e.g., 0111 1011 1011 1010) within dictionary file 106. And when performing such a scanning operation, encoding/decoding process 10 may process 216 the related encoded data file (e.g., related encoded data file 102) utilizing a sampling window, wherein the sampling window may define the size (e.g., in bits or bytes) of the portion of dictionary file that is being scanned for matches with (in this example) result 110. In the example described above, the sampling window is four bits. However, this is for illustrative purposes only and is not intended to be a limitation of this disclosure, as other configurations are possible and are considered to be within the scope of this disclosure. For example, the window may be larger (e.g., 8 bit, 16 bit, 32 bit, 64 bit), which would result in less frequent matches but great benefits when a match is found). Conversely, the window may be smaller (e.g., 2), which would result in more frequent matches but less benefits when a match is found).

And when performing such a scanning operation, encoding/decoding process 10 may process 214 the related encoded data file (e.g., related encoded data file 102) in a bit-wise fashion, where the above-described sampling window is shifted a bit at a time between scans. Conversely and when processing 212 the related encoded data file (e.g., related encoded data file 102) in a byte-wise fashion, the above-described sampling window is shifted a bit at a time between scans.

In computer programming, a bit-wise operation operates on a bit string, a bit array or a binary numeral (considered as a bit string) at the level of its individual bits. It is a fast and simple action, basic to the higher-level arithmetic operations and directly supported by the processor. Most bit-wise operations are presented as two-operand instructions where the result replaces one of the input operands. Conversely, a byte-wise operation operates on a bit string, a bit array or a binary numeral (considered as a bit string) at the level of bytes (i.e., a group of bits). On simple low-cost processors, typically, bit-wise operations are substantially faster than division, several times faster than multiplication, and sometimes significantly faster than addition. While modern processors usually perform addition and multiplication just as fast as bit-wise operations due to their longer instruction pipelines and other architectural design choices, bit-wise operations do commonly use less power because of the reduced use of resources.

High-Level System

Figure 4:
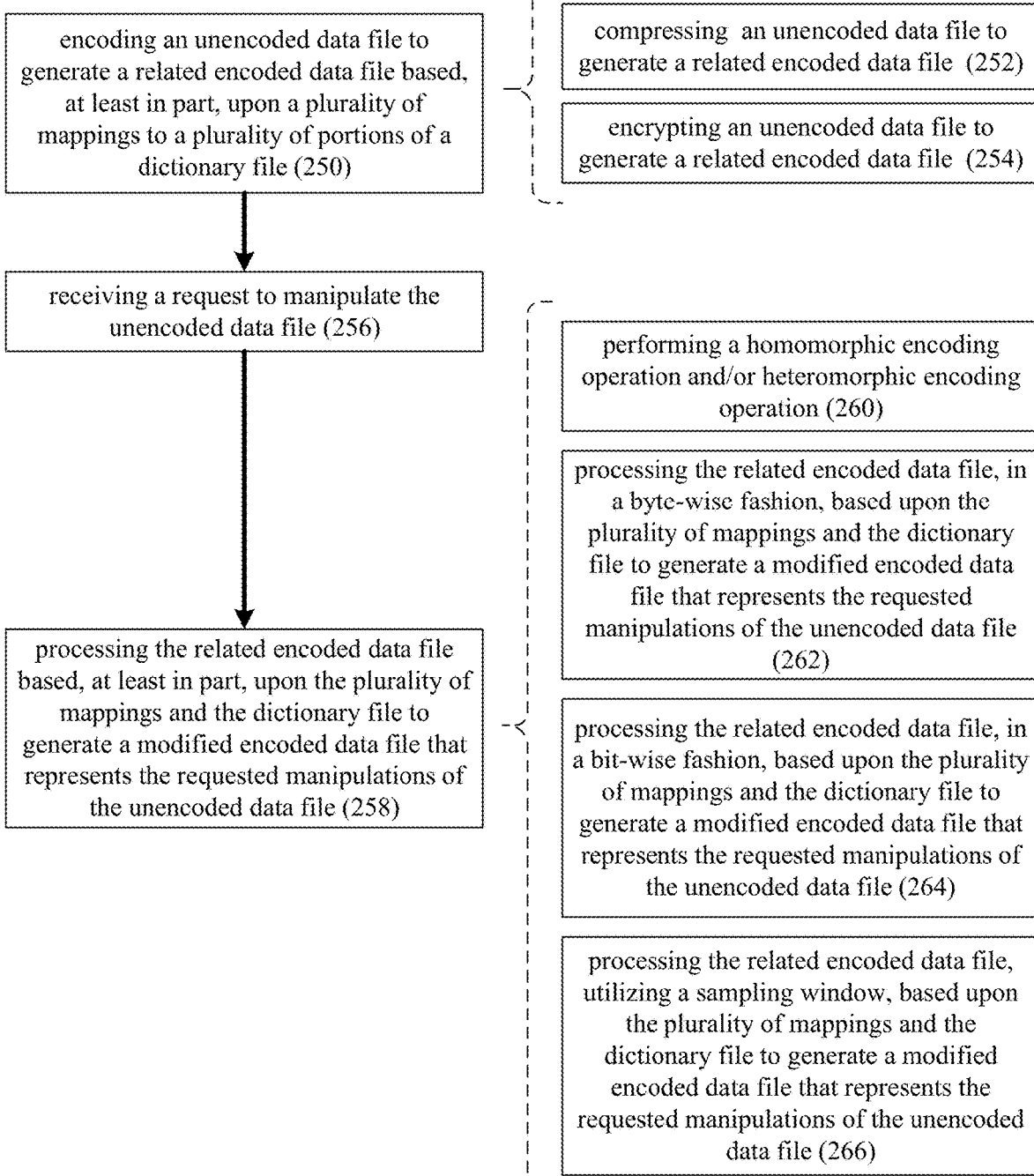
FIG. 4 is a flowchart of the encoding/decoding process of FIG. 1 according to an embodiment of the present disclosure.

The following discussion concerns a more focused view of encoding/decoding process 10. Referring also to FIG. 4, encoding/decoding process 10 may encode 250 an unencoded data file (e.g., first data file 100) to generate a related encoded data file (e.g., related encoded data file 102) based, at least in part, upon a plurality of mappings (e.g., plurality of mappings 104) to a plurality of portions of a dictionary file (e.g., dictionary file 106).

As discussed above, when encoding 250 an unencoded data file (e.g., first data file 100) to generate a related encoded data file (e.g., related encoded data file 102) based, at least in part, upon a plurality of mappings (e.g., plurality of mappings 104) to a plurality of portions of a dictionary file (e.g., dictionary file 106), encoding/decoding process 10 may: compress 252 an unencoded data file (e.g., first data file 100) to generate a related encoded data file (e.g., related encoded data file 102); and/or encrypt 254 an unencoded data file (e.g., first data file 100) to generate a related encoded data file (e.g., related encoded data file 102).

As discussed above, encoding/decoding process 10 may receive 256 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 256 concerned adding twenty-seven to first data file 100.

As discussed above, encoding/decoding process 10 may process 258 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 258 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 260 a homomorphic encoding operation and/or a heteromorphic encoding operation.

As discussed above, when processing 258 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:

process 262 the related encoded data file (e.g., related encoded data file 102), in a byte-wise fashion to generate modified encoded data file 108 (e.g., in the manner described above);

process 264 the related encoded data file (e.g., related encoded data file 102), in a bit-wise fashion to generate modified encoded data file 108 (e.g., in the manner described above); and/or process 266 the related encoded data file (e.g., related encoded data file 102), utilizing a sampling window to generate modified encoded data file 108 (e.g., in the manner described above).

Generic Mapping

Figure 5:
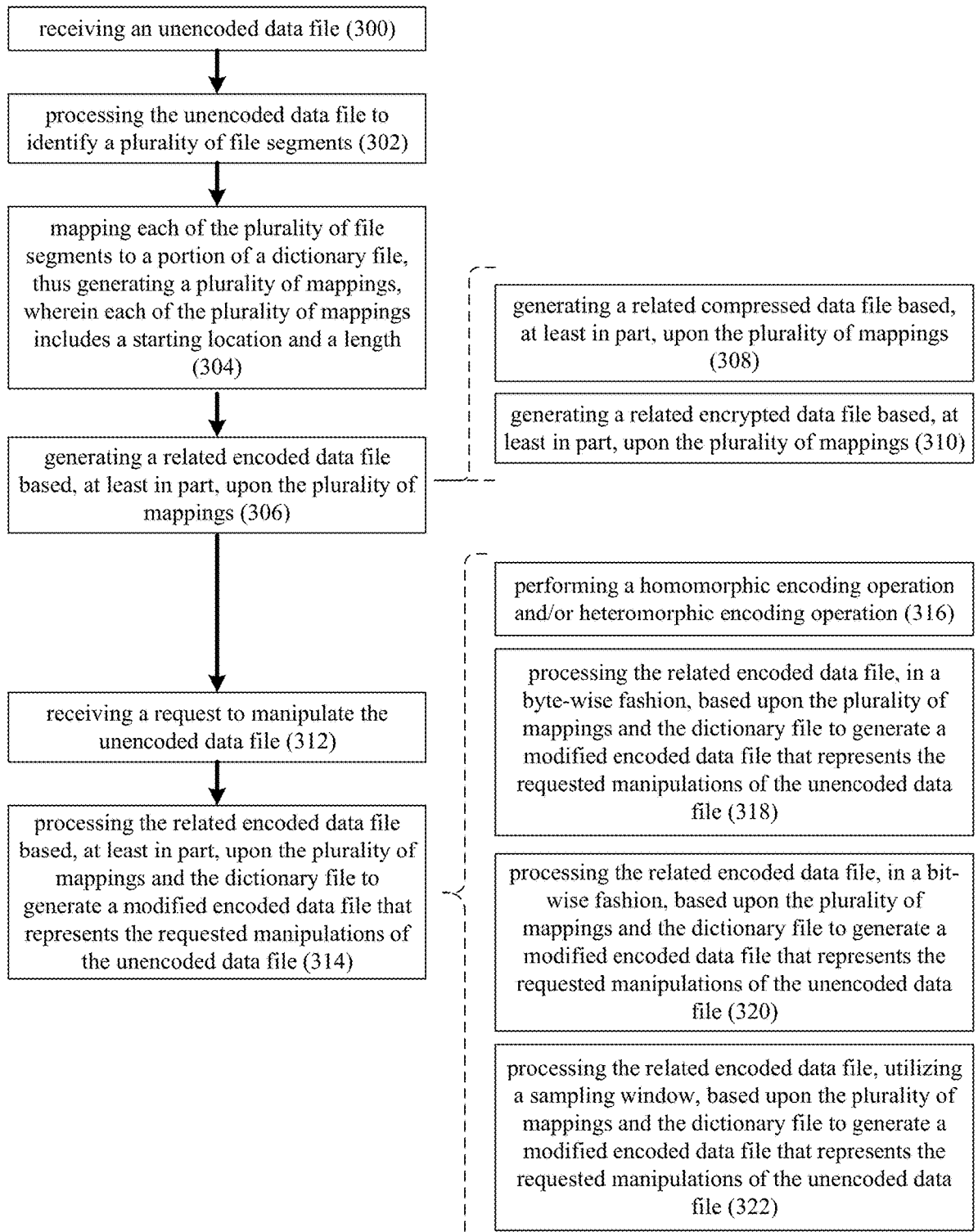
FIG. 5 is a flowchart of the encoding/decoding process of FIG. 1 according to an embodiment of the present disclosure.

The following discussion concerns an overview of mapping within encoding/decoding process 10. Referring also to FIG. 5, encoding/decoding process 10 may receive 300 an unencoded data file (e.g., first data file 100).

Encoding/decoding process 10 may process 302 the unencoded data file (e.g., first data file 100) to identify a plurality of file segments (e.g., plurality of file segments 112). As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111. Encoding/decoding process 10 may map 304 each of the plurality of file segments (e.g., plurality of file segments 112) to a portion of a dictionary file (e.g., dictionary file 106), thus generating a plurality of mappings (e.g., plurality of mappings 104), wherein each of the plurality of mappings (e.g., plurality of mappings 104) may include a starting location and a length.

As discussed above, one example of such mappings may include but is not limited to:

a first mapping <28/4> that defines an offset of 28 bits from the beginning of dictionary file 106 and a read length of 4 bits, thus mapping to 0111 within dictionary file 106;

a second mapping <44/4> that defines an offset of 44 bits from the beginning of dictionary file 106 and a read length of 4 bits, thus mapping to 1011 within dictionary file 106;

a third mapping <36/4> that defines an offset of 36 bits from the beginning of dictionary file 106 and a read length of 4 bits, thus mapping to 1001 within dictionary file 106; and a fourth mapping <60/4> that defines an offset of 60 bits from the beginning of dictionary file 106 and a read length of 4 bits, thus mapping to 1111 within dictionary file 106.

Encoding/decoding process 10 may then generate 306 a related encoded data file (e.g., related encoded data file 102) based, at least in part, upon the plurality of mappings (e.g., plurality of mappings 104). As discussed above and in this example, the related encoded data file (e.g., related encoded data file 102) may include four mappings (e.g., <28/4> <44/4> <36/4> <60/4>).

As discussed above, when generating 306 a related encoded data file (e.g., related encoded data file 102) based, at least in part, upon the plurality of mappings (e.g., plurality of mappings 104), encoding/decoding process 10 may: generate 308 a related compressed data file based, at least in part, upon the plurality of mappings (e.g., plurality of mappings 104); and/or generate 310 a related encrypted data file based, at least in part, upon the plurality of mappings (e.g., plurality of mappings 104).

Encoding/decoding process 10 may receive 312 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 312 concerned adding twenty-seven to first data file 100.

Encoding/decoding process 10 may process 314 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 314 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 316 a homomorphic encoding operation; and/or a heteromorphic encoding operation.

When processing 314 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/ decoding process 10 may:

process 318 the related encoded data file (e.g., related encoded data file 102), in a byte-wise fashion to generate modified encoded data file 108 (e.g., in the manner described above);

process 320 the related encoded data file (e.g., related encoded data file 102), in a bit-wise fashion to generate modified encoded data file 108 (e.g., in the manner described above); and/or process 322 the related encoded data file (e.g., related encoded data file 102), utilizing a sampling window to generate modified encoded data file 108 (e.g., in the manner described above).

Homomorphic

Figure 6:
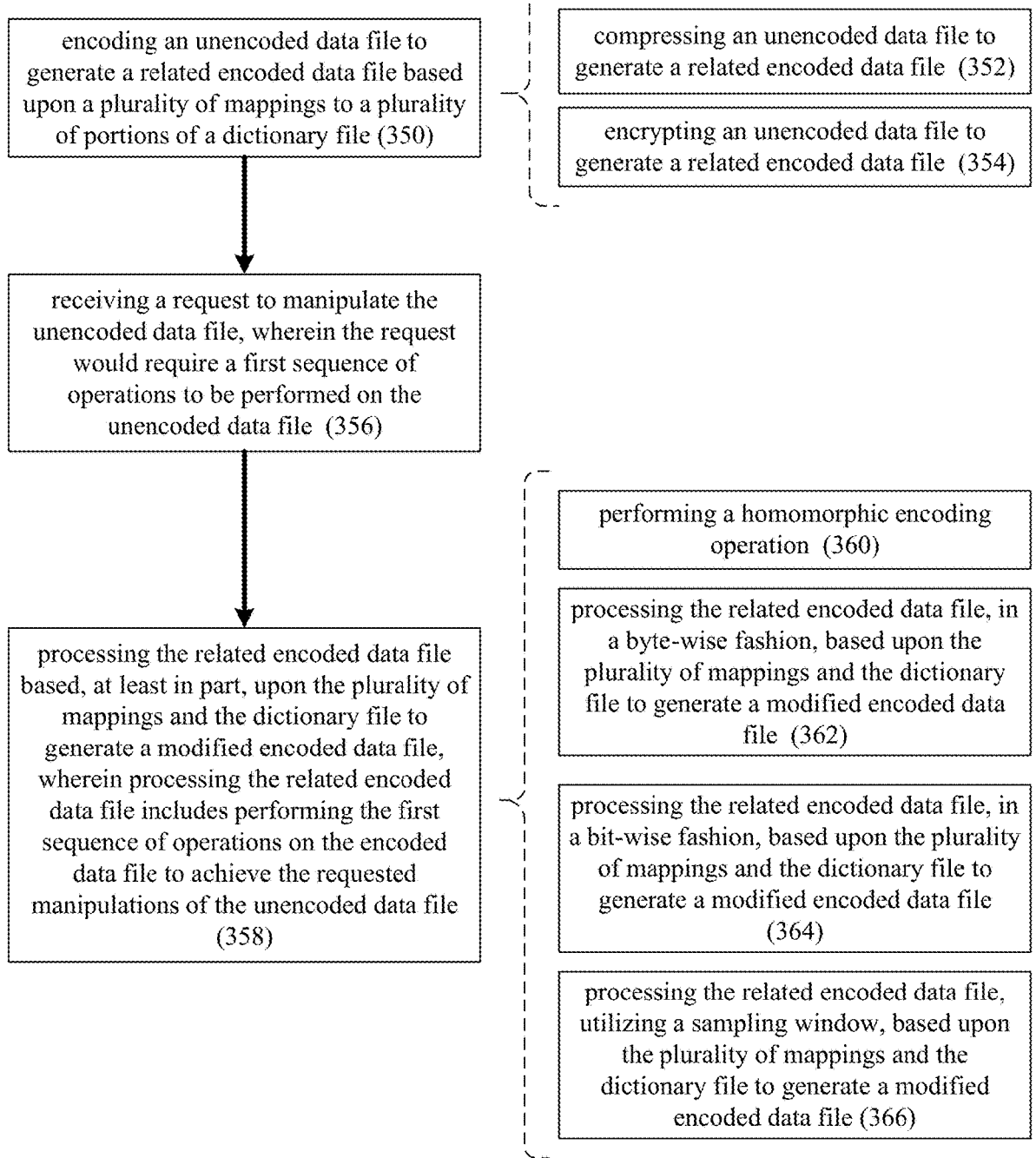
FIG. 6 is a flowchart of the encoding/decoding process of FIG. 1 according to an embodiment of the present disclosure.

The following discussion concerns an overview of homomorphic encoding within encoding/decoding process 10. Referring also to FIG. 6, encoding/decoding process 10 may encode 350 an unencoded data file (e.g., first data file 100) to generate a related encoded data file (e.g., related encoded data file 102) based upon a plurality of mappings (e.g., plurality of mappings 104) to a plurality of portions of a dictionary file (e.g., dictionary file 106).

As discussed above, when encoding 350 an unencoded data file (e.g., first data file 100) to generate a related encoded data file (e.g., related encoded data file 102) based upon a plurality of mappings (e.g., plurality of mappings 104) to a plurality of portions of a dictionary file (e.g., dictionary file 106), encoding/decoding process 10 may: compress 352 an unencoded data file (e.g., first data file 100) to generate a related encoded data file (e.g., related encoded data file 102).

When encoding 350 an unencoded data file (e.g., first data file 100) to generate a related encoded data file (e.g., related encoded data file 102) based upon a plurality of mappings (e.g., plurality of mappings 104) to a plurality of portions of a dictionary file (e.g., dictionary file 106), encoding/decoding process 10 may: encrypt 354 an unencoded data file (e.g., first data file 100) to generate a related encoded data file (e.g., related encoded data file 102).

Encoding/decoding process 10 may receive 356 a request (e.g., request 160) to manipulate the unencoded data file (e.g., first data file 100), wherein the request (e.g., request 160) would require a first sequence of operations to be performed on the unencoded data file (e.g., first data file 100). The requested manipulations may concern one or more of: a computation operation; a search operation; an append operation; a splitting operation; a joining operation; and a concatenating operation. In the example discussed above, the request (e.g., request 160) received 356 concerned adding twenty-seven to first data file 100.

Encoding/decoding process 10 may process 358 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108), wherein processing the related encoded data file (e.g., related encoded data file 102) may include performing the first sequence of operations on the encoded data file to achieve the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 358 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108), encoding/decoding process 10 may: perform 360 a homomorphic encoding operation.

When processing 358 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108), encoding/decoding process 10 may:

- process 362 the related encoded data file (e.g., related encoded data file 102), in a byte-wise fashion to generate modified encoded data file 108 (e.g., in the manner described above);
- process 364 the related encoded data file (e.g., related encoded data file 102), in a bit-wise fashion to generate modified encoded data file 108 (e.g., in the manner described above); and/or
- process 366 the related encoded data file (e.g., related encoded data file 102), utilizing a sampling window to generate modified encoded data file 108 (e.g., in the manner described above).

Heteromorphic

Figure 7:
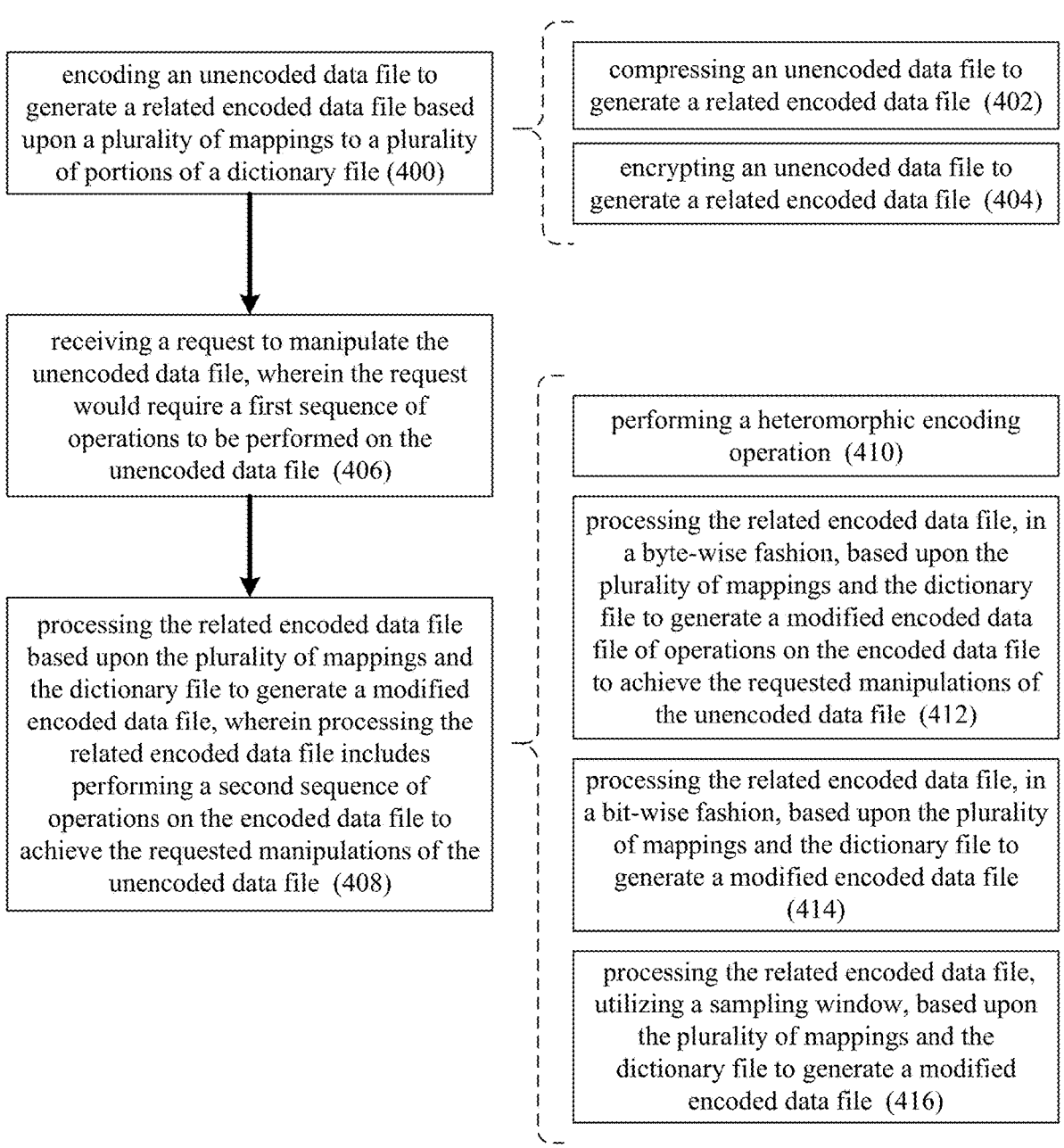
FIG. 7 is a flowchart of the encoding/decoding process of FIG. 1 according to an embodiment of the present disclosure.

The following discussion concerns an overview of heteromorphic encoding within encoding/decoding process 10. Referring also to FIG. 7, encoding/decoding process 10 may encode 400 an unencoded data file (e.g., first data file 100) to generate a related encoded data file (e.g., related encoded data file 102) based upon a plurality of mappings (e.g., plurality of mappings 104) to a plurality of portions of a dictionary file (e.g., dictionary file 106).

As discussed above, when encoding 400 an unencoded data file (e.g., first data file 100) to generate a related encoded data file (e.g., related encoded data file 102) based upon a plurality of mappings (e.g., plurality of mappings 104) to a plurality of portions of a dictionary file (e.g., dictionary file 106), encoding/decoding process 10 may: compress 402 an unencoded data file (e.g., first data file 100) to generate a related encoded data file (e.g., related encoded data file 102).

When encoding 400 an unencoded data file (e.g., first data file 100) to generate a related encoded data file (e.g., related encoded data file 102) based upon a plurality of mappings (e.g., plurality of mappings 104) to a plurality of portions of a dictionary file (e.g., dictionary file 106), encoding/decoding process 10 may: encrypt 404 an unencoded data file (e.g., first data file 100) to generate a related encoded data file (e.g., related encoded data file 102).

Encoding/decoding process 10 may receive 406 a request (e.g., request 160) to manipulate the unencoded data file (e.g., first data file 100), wherein the request (e.g., request 160) would require a first sequence of operations to be performed on the unencoded data file (e.g., first data file 100). The requested manipulations may concern one or more of: a computation operation; a search operation; an append operation; a splitting operation; a joining operation; and a concatenating operation. In the example discussed above, the request (e.g., request 160) received 406 concerned adding twenty-seven to first data file 100.

Encoding/decoding process 10 may process 408 the related encoded data file (e.g., related encoded data file 102) based upon the plurality of mappings (e.g., plurality of mappings 104) and the dictionary file (e.g., dictionary file 106) to generate a modified encoded data file (e.g., modified encoded data file 108), wherein processing the related encoded data file (e.g., related encoded data file 102) may include performing a second sequence of operations on the encoded data file to achieve the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As this is a heteromorphic encoding operation, the second sequence of operations cannot be identical to the first sequence of operations, as that would yield a homomorphic encoding operation. Accordingly, this second sequence of operations may be dissimilar (or only partially similar) to the first sequence of operations, as this is a heteromorphic encoding operation.

As discussed above, when processing 408 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108), encoding/decoding process 10 may: perform 410 a heteromorphic encoding operation.

When processing 408 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108), encoding/decoding process 10 may:

- process 412 the related encoded data file (e.g., related encoded data file 102), in a byte-wise fashion to generate modified encoded data file 108 (e.g., in the manner described above);
- process 414 the related encoded data file (e.g., related encoded data file 102), in a bit-wise fashion to generate modified encoded data file 108 (e.g., in the manner described above); and/or
- process 416 the related encoded data file (e.g., related encoded data file 102), utilizing a sampling window to generate modified encoded data file 108 (e.g., in the manner described above).

Encoded Data (in Transit)

Figure 8:
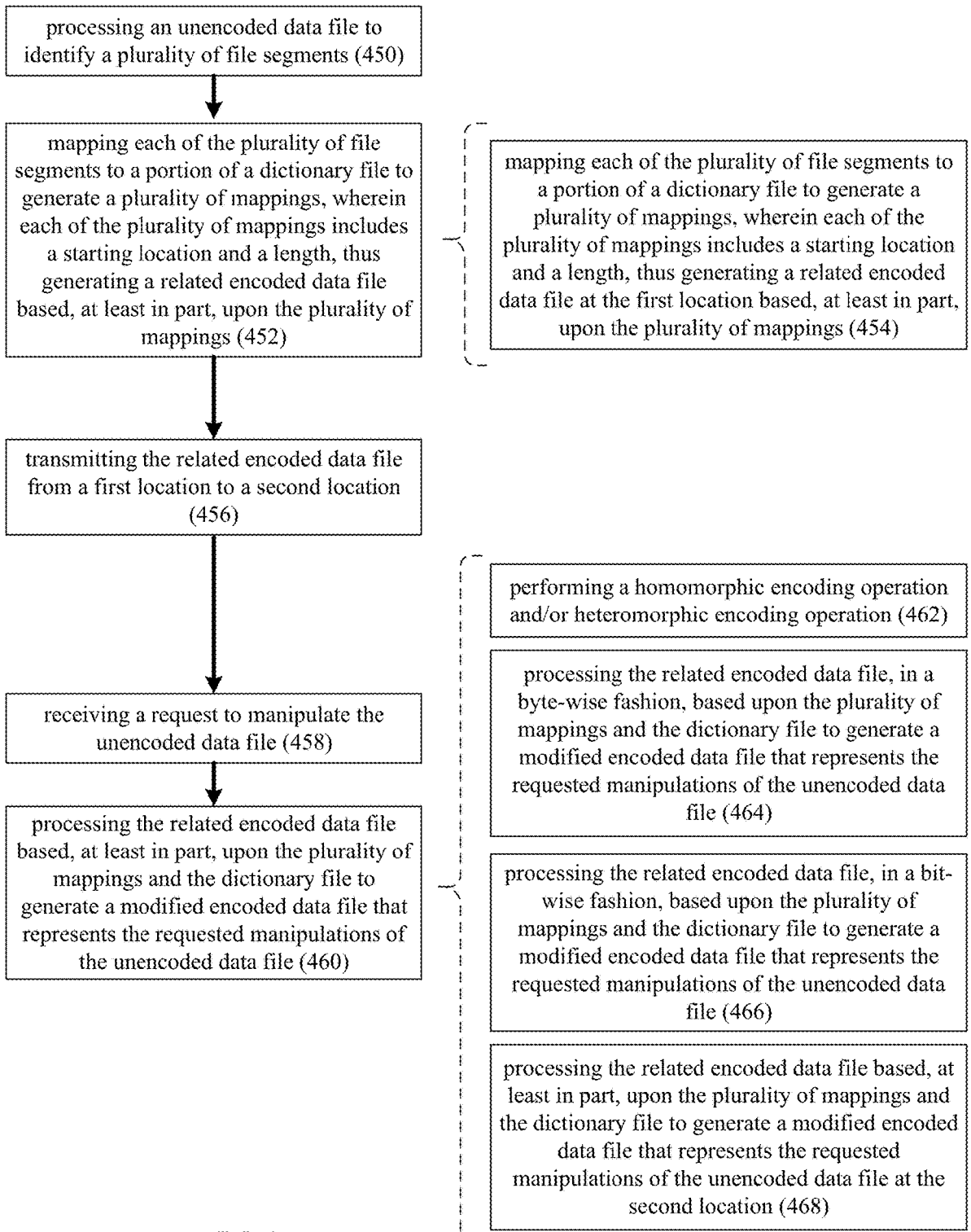
FIG. 8 is a flowchart of the encoding/decoding process of FIG. 1 according to an embodiment of the present disclosure.

The following discussion concerns a use case for encoding/decoding process 10 concerning encoded data in transit. Referring also to FIG. 8, encoding/decoding process 10 may process 450 an unencoded data file (e.g., first data file 100) to identify a plurality of file segments (e.g., plurality of file segments 112).

As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111.

Encoding/decoding process 10 may map 452 each of the plurality of file segments (e.g., plurality of file segments 112) to a portion of a dictionary file (e.g., dictionary file 106) to generate a plurality of mappings (e.g., plurality of mappings 104), wherein each of the plurality of mappings (e.g., plurality of mappings 104) may include a starting location and a length, thus generating a related encoded data file (e.g., related encoded data file 102) based, at least in part, upon the plurality of mappings (e.g., plurality of mappings 104).

As discussed above, one example of such mappings may include but is not limited to:

a first mapping <28/4> that defines an offset of 28 bits from the beginning of dictionary file 106 and a read length of 4 bits, thus mapping to 0111 within dictionary file 106;

a second mapping <44/4> that defines an offset of 44 bits from the beginning of dictionary file 106 and a read length of 4 bits, thus mapping to 1011 within dictionary file 106;

a third mapping <36/4> that defines an offset of 36 bits from the beginning of dictionary file 106 and a read length of 4 bits, thus mapping to 1001 within dictionary file 106; and a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>).

When mapping 452 each of the plurality of file segments (e.g., plurality of file segments 112) to a portion of a dictionary file (e.g., dictionary file 106) to generate a plurality of mappings (e.g., plurality of mappings 104), wherein each of the plurality of mappings (e.g., plurality of mappings 104) may include a starting location and a length, thus generating a related encoded data file (e.g., related encoded data file 102) based, at least in part, upon the plurality of mappings (e.g., plurality of mappings 104), encoding/decoding process 10 may: map 454 each of the plurality of file segments (e.g., plurality of file segments 112) to a portion of a dictionary file (e.g., dictionary file 106) to generate a plurality of mappings (e.g., plurality of mappings 104), wherein each of the plurality of mappings (e.g., plurality of mappings 104) may include a starting location and a length, thus generating a related encoded data file (e.g., related encoded data file 102) at a first location (e.g., first location 114) based, at least in part, upon the plurality of mappings (e.g., plurality of mappings 104).

Encoding/decoding process 10 may transmit 456 the related encoded data file (e.g., related encoded data file 102) from the first location (e.g., first location 114) to a second location (e.g., second location 116). Examples of such a first location (e.g., first location 114) may include but are not limited to: the location at which related encoded data file 102 is generated or initially stored. Examples of such a second location (e.g., second location 116) may include but are not limited to: the location to which related encoded data file 102 is transmitted or subsequently stored.

Encoding/decoding process 10 may receive 458 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 256 concerned adding twenty-seven to first data file 100.

Encoding/decoding process 10 may process 460 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 460 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 462 a homomorphic encoding operation and/or a heteromorphic encoding operation.

When processing 460 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:

process 464 the related encoded data file (e.g., related encoded data file 102), in a byte-wise fashion to generate modified encoded data file 108 (e.g., in the manner described above); and/or process 466 the related encoded data file (e.g., related encoded data file 102), in a bit-wise fashion to generate modified encoded data file 108 (e.g., in the manner described above).

When processing 460 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: process 468 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100) at the second location (e.g., second location 116).

Encoded Data (in Transit Short-Range Wireless)

Figure 9:
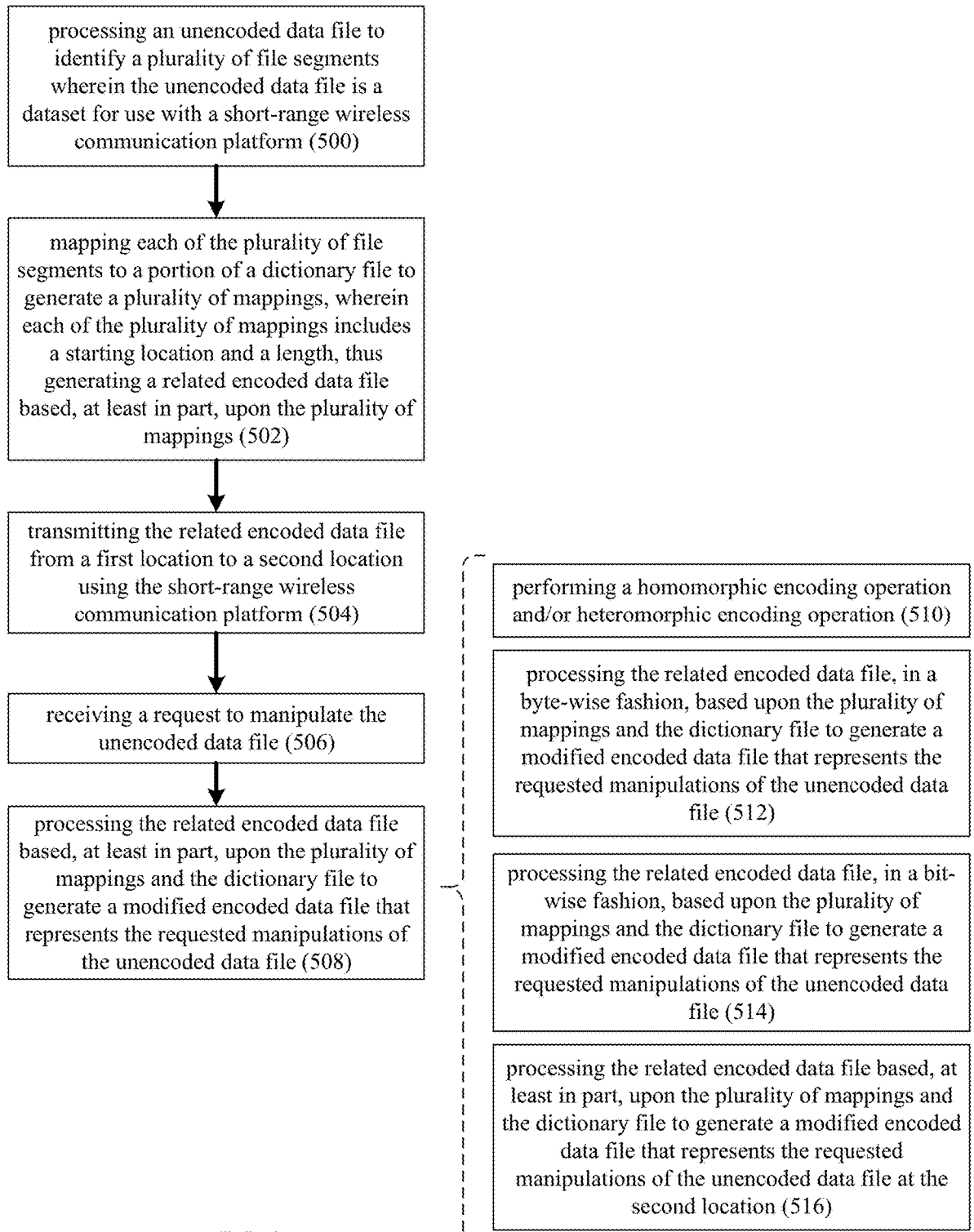
FIG. 9 is a flowchart of the encoding/decoding process of FIG. 1 according to an embodiment of the present disclosure.

The following discussion concerns a use case for encoding/decoding process 10 concerning encoded data in transit with short-range wireless. Referring also to FIG. 9, encoding/decoding process 10 may process 500 an unencoded data file (e.g., first data file 100) to identify a plurality of file segments (e.g., plurality of file segments 112).

As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111.

The unencoded data file (e.g., first data file 100) may be a dataset for use with a short-range wireless communication platform (e.g., short-range wireless communication platform 118). Examples of this short-range wireless communication platform (e.g., short-range wireless communication platform 118) may include one or more of: a Bluetooth short-range wireless communication platform; and a Wi-Fi short-range wireless communication platform.

As is known in the art, Bluetooth is a short-range wireless technology standard that is used for exchanging data between fixed and mobile devices over short distances and building personal area networks (PANs). It employs UHF radio waves in the ISM bands, from 2.402 GHz to 2.48 GHz. It is mainly used as an alternative to wire connections, to exchange files between nearby portable devices and connect cell phones and music players with wireless headphones. In the most widely used mode, transmission power is limited to 2.5 milliwatts, giving it a very short range of up to 10 metres (33 ft).

As is known in the art, Wi-Fi is a family of wireless network protocols, based on the IEEE 802.11 family of standards, which are commonly used for local area networking of devices and Internet access, allowing nearby digital devices to exchange data by radio waves. These are the most widely used computer networks in the world, used globally in home and small office networks to link desktop and laptop computers, tablet computers, smartphones, smart TVs, printers, and smart speakers together and to a wireless router to connect them to the Internet, and in wireless access points in public places like coffee shops, hotels, libraries and airports to provide the public Internet access for mobile devices.

Encoding/decoding process 10 may map 502 each of the plurality of file segments (e.g., plurality of file segments 112) to a portion of a dictionary file (e.g., dictionary file 106) to generate a plurality of mappings (e.g., plurality of mappings 104), wherein each of the plurality of mappings (e.g., plurality of mappings 104) may include a starting location and a length, thus generating a related encoded data file (e.g., related encoded data file 102) based, at least in part, upon the plurality of mappings (e.g., plurality of mappings 104).

As discussed above, one example of such mappings may include but is not limited to:

- a first mapping <28/4> that defines an offset of 28 bits from the beginning of dictionary file 106 and a read length of 4 bits, thus mapping to 0111 within dictionary file 106;
- a second mapping <44/4> that defines an offset of 44 bits from the beginning of dictionary file 106 and a read length of 4 bits, thus mapping to 1011 within dictionary file 106;
- a third mapping <36/4> that defines an offset of 36 bits from the beginning of dictionary file 106 and a read length of 4 bits, thus mapping to 1001 within dictionary file 106; and
- a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>).

Encoding/decoding process 10 may transmit 504 the related encoded data file (e.g., related encoded data file 102) from a first location (e.g., first location 114) to a second location (e.g., second location 116) using the short-range wireless communication platform (e.g., short-range wireless communication platform 118). Examples of such a first location (e.g., first location 114) may include but are not limited to: the location at which related encoded data file 102 is generated or initially stored. Examples of such a second location (e.g., second location 116) may include but are not limited to: the location to which related encoded data file 102 is transmitted or subsequently stored.

Encoding/decoding process 10 may receive 506 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 506 concerned adding twenty-seven to first data file 100.

Encoding/decoding process 10 may process 508 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 508 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 510 a homomorphic encoding operation and/or a heteromorphic encoding operation.

When processing 508 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:

- process 512 the related encoded data file (e.g., related encoded data file 102), in a byte-wise fashion to generate modified encoded data file 108 (e.g., in the manner described above); and/or
- process 514 the related encoded data file (e.g., related encoded data file 102), in a bit-wise fashion to generate modified encoded data file 108 (e.g., in the manner described above).

When processing 508 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: process 516 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100) at the second location (e.g., second location 116).

Encoded Data (in Transit Long-Range Wireless)

Figure 10:
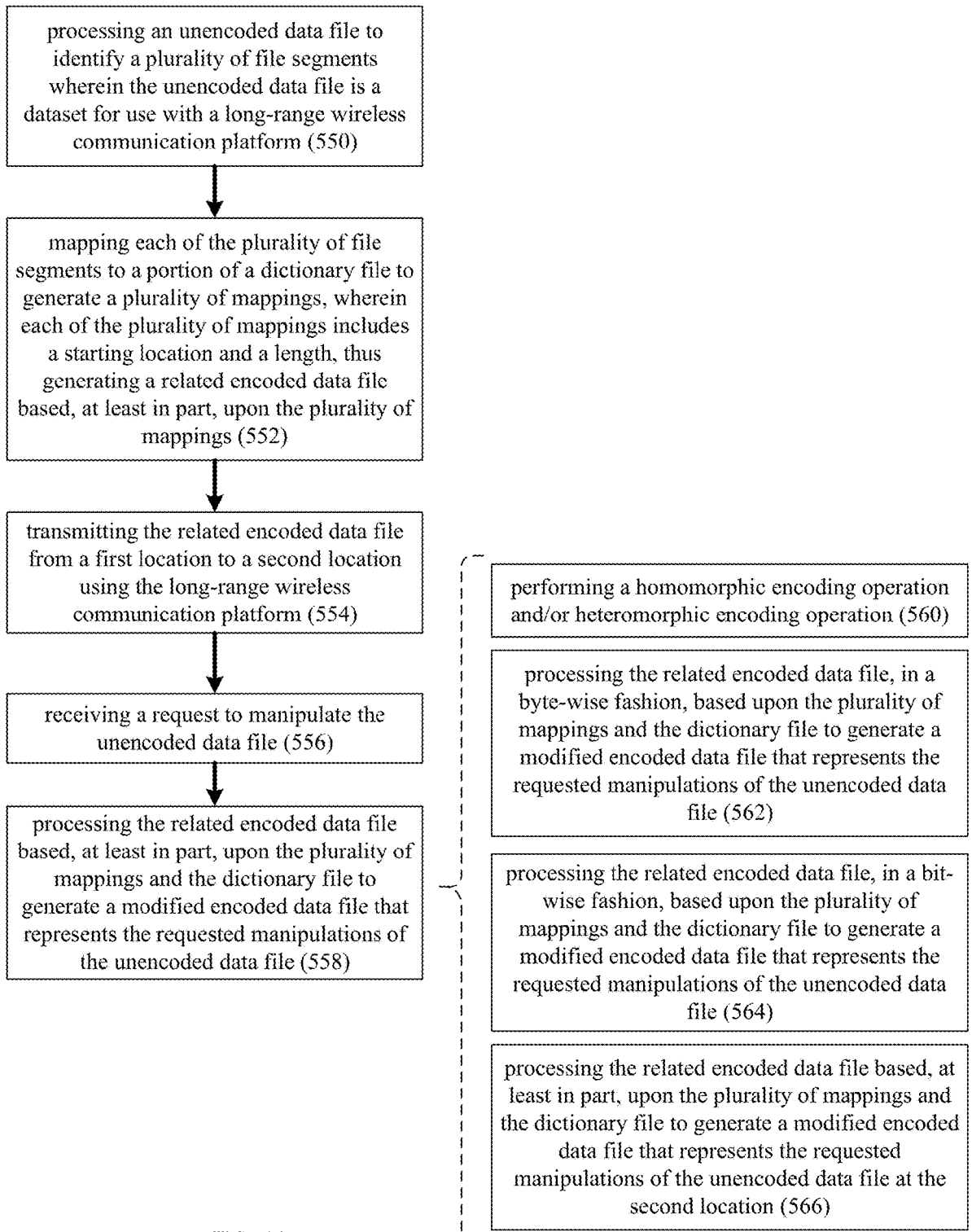
FIG. 10 is a flowchart of the encoding/decoding process of FIG. 1 according to an embodiment of the present disclosure.

The following discussion concerns a use case for encoding/decoding process 10 concerning encoded data in transit with long-range wireless. Referring also to FIG. 10, encoding/decoding process 10 may process 550 an unencoded data file (e.g., first data file 100) to identify a plurality of file segments (e.g., plurality of file segments 112).

As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111.

The unencoded data file (e.g., first data file 100) may be a dataset for use with a long-range wireless communication platform (e.g., long-range wireless communication platform 120). Examples of this long-range wireless communication platform (e.g., long-range wireless communication platform 120) may include one or more of: a cellular-based long-range wireless communication platform; a microwave-based long-range wireless communication platform; and a satellite-based long-range wireless communication platform.

Encoding/decoding process 10 may map 552 each of the plurality of file segments (e.g., plurality of file segments 112) to a portion of a dictionary file (e.g., dictionary file 106) to generate a plurality of mappings (e.g., plurality of mappings 104), wherein each of the plurality of mappings (e.g., plurality of mappings 104) may include a starting location and a length, thus generating a related encoded data file (e.g., related encoded data file 102) based, at least in part, upon the plurality of mappings (e.g., plurality of mappings 104).

As discussed above, one example of such mappings may include but is not limited to:

a first mapping <28/4> that defines an offset of 28 bits from the beginning of dictionary file 106 and a read length of 4 bits, thus mapping to 0111 within dictionary file 106;

a second mapping <44/4> that defines an offset of 44 bits from the beginning of dictionary file 106 and a read length of 4 bits, thus mapping to 1011 within dictionary file 106;

a third mapping <36/4> that defines an offset of 36 bits from the beginning of dictionary file 106 and a read length of 4 bits, thus mapping to 1001 within dictionary file 106; and a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>).

Encoding/decoding process 10 may transmit 554 the related encoded data file (e.g., related encoded data file 102) from a first location (e.g., first location 114) to a second location (e.g., second location 116) using the long-range wireless communication platform (e.g., long-range wireless communication platform 120). Examples of such a first location (e.g., first location 114) may include but are not limited to: the location at which related encoded data file 102 is generated or initially stored. Examples of such a second location (e.g., second location 116) may include but are not limited to: the location to which related encoded data file 102 is transmitted or subsequently stored.

Encoding/decoding process 10 may receive 556 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 556 concerned adding twenty-seven to first data file 100.

Encoding/decoding process 10 may process 558 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 558 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 560 a homomorphic encoding operation and/or a heteromorphic encoding operation.

When processing 558 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:

process 562 the related encoded data file (e.g., related encoded data file 102), in a byte-wise fashion to generate modified encoded data file 108 (e.g., in the manner described above); and/or process 564 the related encoded data file (e.g., related encoded data file 102), in a bit-wise fashion to generate modified encoded data file 108 (e.g., in the manner described above).

When processing 558 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: process 566 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100) at the second location (e.g., second location 116).

Encoded Data (in Transit Direct Coupled)

Figure 11:
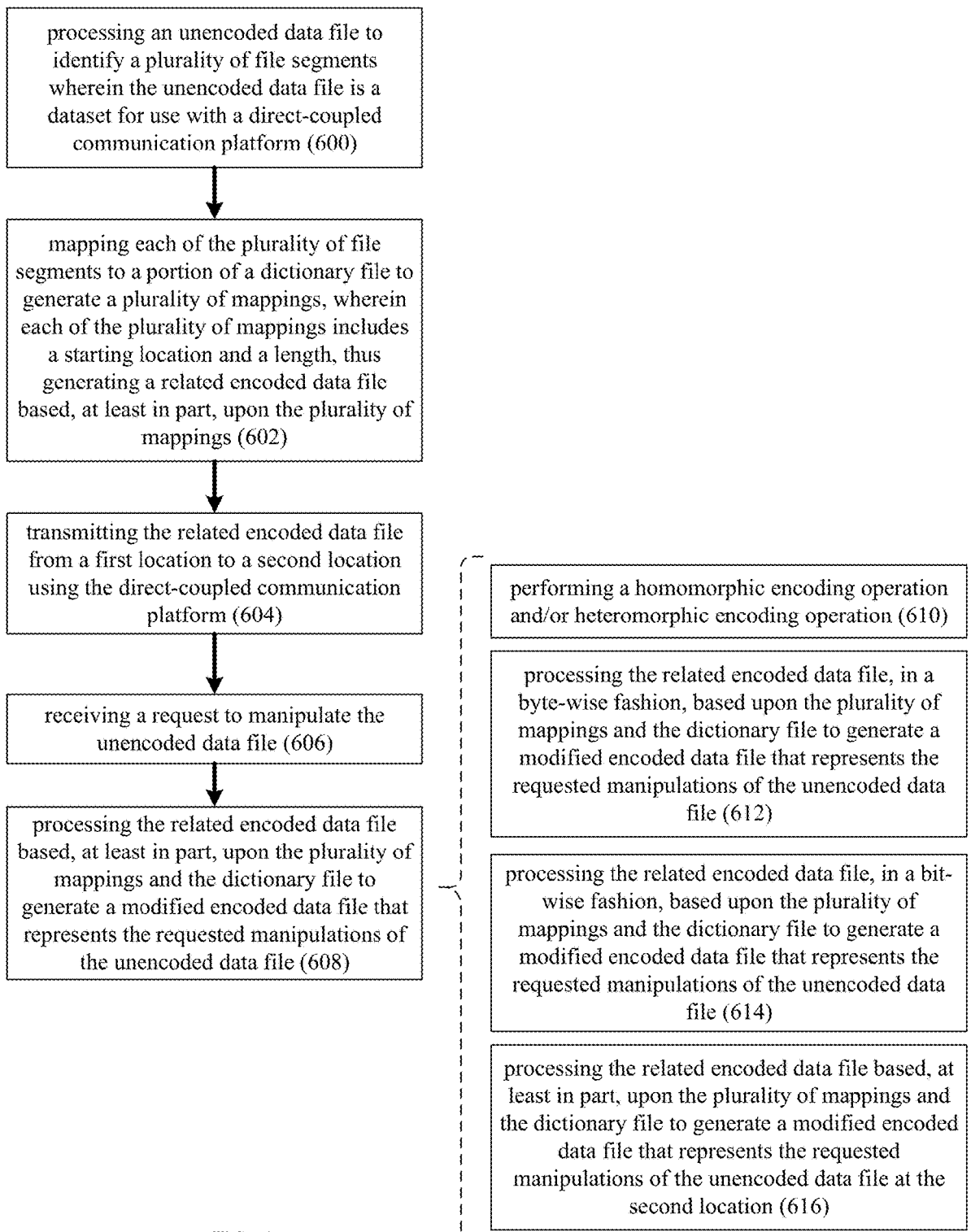
FIG. 11 is a flowchart of the encoding/decoding process of FIG. 1 according to an embodiment of the present disclosure.

The following discussion concerns a use case for encoding/decoding process 10 concerning encoded data in transit with direct coupling. Referring also to FIG. 11, encoding/decoding process 10 may process 600 an unencoded data file (e.g., first data file 100) to identify a plurality of file segments (e.g., plurality of file segments 112).

As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111.

The unencoded data file (e.g., first data file 100) may be a dataset for use with a direct-coupled communication platform (e.g., direct-coupled communication platform 122). Examples of the direct-coupled communication platform (e.g., direct-coupled communication platform 122) may include one or more of: a copper-based direct-coupled communication platform (e.g., a platform that utilizes coaxial cables); a twisted pair-based direct-coupled communication platform (e.g., a platform that utilizes twisted conductor cables); and an optical-based direct-coupled communication platform (e.g., a platform that utilizes fiber-optic cables).

Encoding/decoding process 10 may map 602 each of the plurality of file segments (e.g., plurality of file segments 112) to a portion of a dictionary file (e.g., dictionary file 106) to generate a plurality of mappings (e.g., plurality of mappings 104), wherein each of the plurality of mappings (e.g., plurality of mappings 104) may include a starting location and a length, thus generating a related encoded data file (e.g., related encoded data file 102) based, at least in part, upon the plurality of mappings (e.g., plurality of mappings 104).

As discussed above, one example of such mappings may include but is not limited to:

- a first mapping <28/4> that defines an offset of 28 bits from the beginning of dictionary file 106 and a read length of 4 bits, thus mapping to 0111 within dictionary file 106;
- a second mapping <44/4> that defines an offset of 44 bits from the beginning of dictionary file 106 and a read length of 4 bits, thus mapping to 1011 within dictionary file 106;
- a third mapping <36/4> that defines an offset of 36 bits from the beginning of dictionary file 106 and a read length of 4 bits, thus mapping to 1001 within dictionary file 106; and
- a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>).

Encoding/decoding process 10 may transmit 604 the related encoded data file (e.g., related encoded data file 102) from a first location (e.g., first location 114) to a second location (e.g., second location 116) using the direct-coupled communication platform (e.g., direct-coupled communication platform 122). Examples of such a first location (e.g., first location 114) may include but are not limited to: the location at which related encoded data file 102 is generated or initially stored. Examples of such a second location (e.g., second location 116) may include but are not limited to: the location to which related encoded data file 102 is transmitted or subsequently stored.

Encoding/decoding process 10 may receive 606 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 606 concerned adding twenty-seven to first data file 100.

Encoding/decoding process 10 may process 608 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 608 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 610 a homomorphic encoding operation; and/or a heteromorphic encoding operation.

When processing 608 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:

- process 612 the related encoded data file (e.g., related encoded data file 102), in a byte-wise fashion to generate modified encoded data file 108 (e.g., in the manner described above); and/or
- process 614 the related encoded data file (e.g., related encoded data file 102), in a bit-wise fashion to generate modified encoded data file 108 (e.g., in the manner described above).

When processing 608 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: process 616 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100) at the second location (e.g., second location 116).

Encoded Data (in Transit Satellite-Based Wireless)

Figure 12:
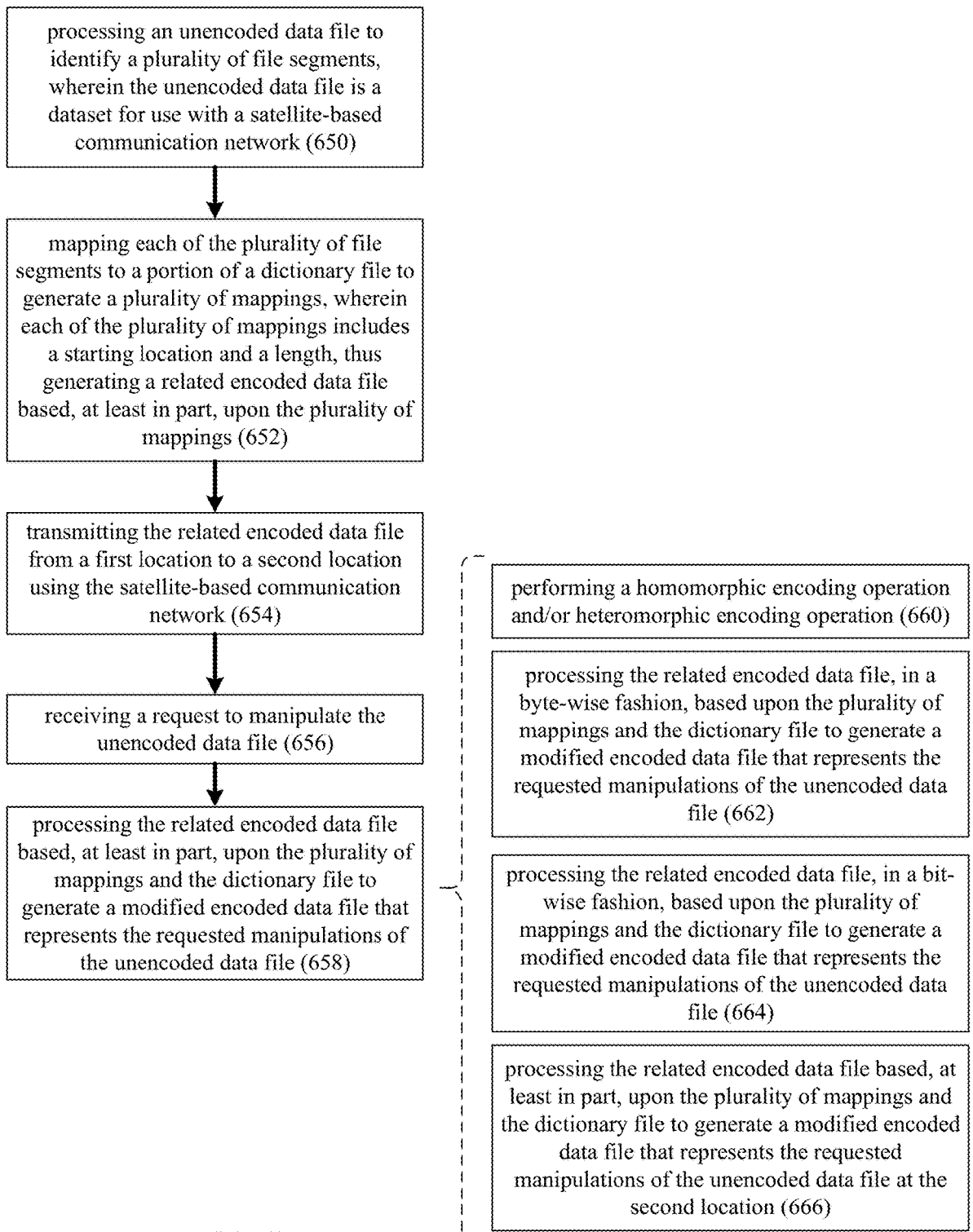
FIG. 12 is a flowchart of the encoding/decoding process of FIG. 1 according to an embodiment of the present disclosure.

The following discussion concerns a use case for encoding/decoding process 10 concerning encoded data in transit with satellite-based wireless. Referring also to FIG. 12, encoding/decoding process 10 may process 650 an unencoded data file (e.g., first data file 100) to identify a plurality of file segments (e.g., plurality of file segments 112).

As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111.

The unencoded data file (e.g., first data file 100) may be a dataset for use with a satellite-based communication network (e.g., satellite-based communication network 124). Examples of the satellite-based communication network (e.g., satellite-based communication network 124) may include one or more of:
- an internet communication network including one or more satellites that is configured to e.g., provide internet connectivity to individuals and businesses;
- a mesh communication network including one or more satellites that is configured to e.g., provide geographically-dispersed connectivity to individuals and businesses;
- a telephone communication network including one or more satellites that is configured to e.g., provide telephone connectivity to individuals and businesses;
- an entertainment communication network including one or more satellites that is configured to e.g., provide entertainment connectivity to individuals and businesses;
- a surface-to-satellite communication network including one or more satellites that is configured to e.g., provide satellite uplink connectivity to individuals and businesses;
- a satellite-to-satellite communication network including one or more satellites that is configured to e.g., provide satellite interlink connectivity to individuals and businesses; and
- a satellite-to-surface communication network including one or more satellites that is configured to e.g., provide satellite downlink connectivity to individuals and businesses.

Encoding/decoding process 10 may map 652 each of the plurality of file segments (e.g., plurality of file segments 112) to a portion of a dictionary file (e.g., dictionary file 106) to generate a plurality of mappings (e.g., plurality of mappings 104), wherein each of the plurality of mappings (e.g., plurality of mappings 104) may include a starting location and a length, thus generating a related encoded data file (e.g., related encoded data file 102) based, at least in part, upon the plurality of mappings (e.g., plurality of mappings 104).

As discussed above, one example of such mappings may include but is not limited to:
- a first mapping <28/4> that defines an offset of 28 bits from the beginning of dictionary file 106 and a read length of 4 bits, thus mapping to 0111 within dictionary file 106;
- a second mapping <44/4> that defines an offset of 44 bits from the beginning of dictionary file 106 and a read length of 4 bits, thus mapping to 1011 within dictionary file 106;
- a third mapping <36/4> that defines an offset of 36 bits from the beginning of dictionary file 106 and a read length of 4 bits, thus mapping to 1001 within dictionary file 106; and
- a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>).

Encoding/decoding process 10 may transmit 654 the related encoded data file (e.g., related encoded data file 102) from a first location (e.g., first location 114) to a second location (e.g., second location 116) using the satellite-based communication network (e.g., satellite-based communication network 124). Examples of such a first location (e.g., first location 114) may include but are not limited to: the location at which related encoded data file 102 is generated or initially stored. Examples of such a second location (e.g., second location 116) may include but are not limited to: the location to which related encoded data file 102 is transmitted or subsequently stored.

Encoding/decoding process 10 may receive 656 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 656 concerned adding twenty-seven to first data file 100.

Encoding/decoding process 10 may process 658 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 658 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 660 a homomorphic encoding operation and/or a heteromorphic encoding operation.

When processing 658 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:
- process 662 the related encoded data file (e.g., related encoded data file 102), in a byte-wise fashion to generate modified encoded data file 108 (e.g., in the manner described above); and/or
- process 664 the related encoded data file (e.g., related encoded data file 102), in a bit-wise fashion to generate modified encoded data file 108 (e.g., in the manner described above).

When processing 658 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: process 666 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100) at the second location (e.g., second location 116).

Encoded Data (at Rest)

Figure 13:
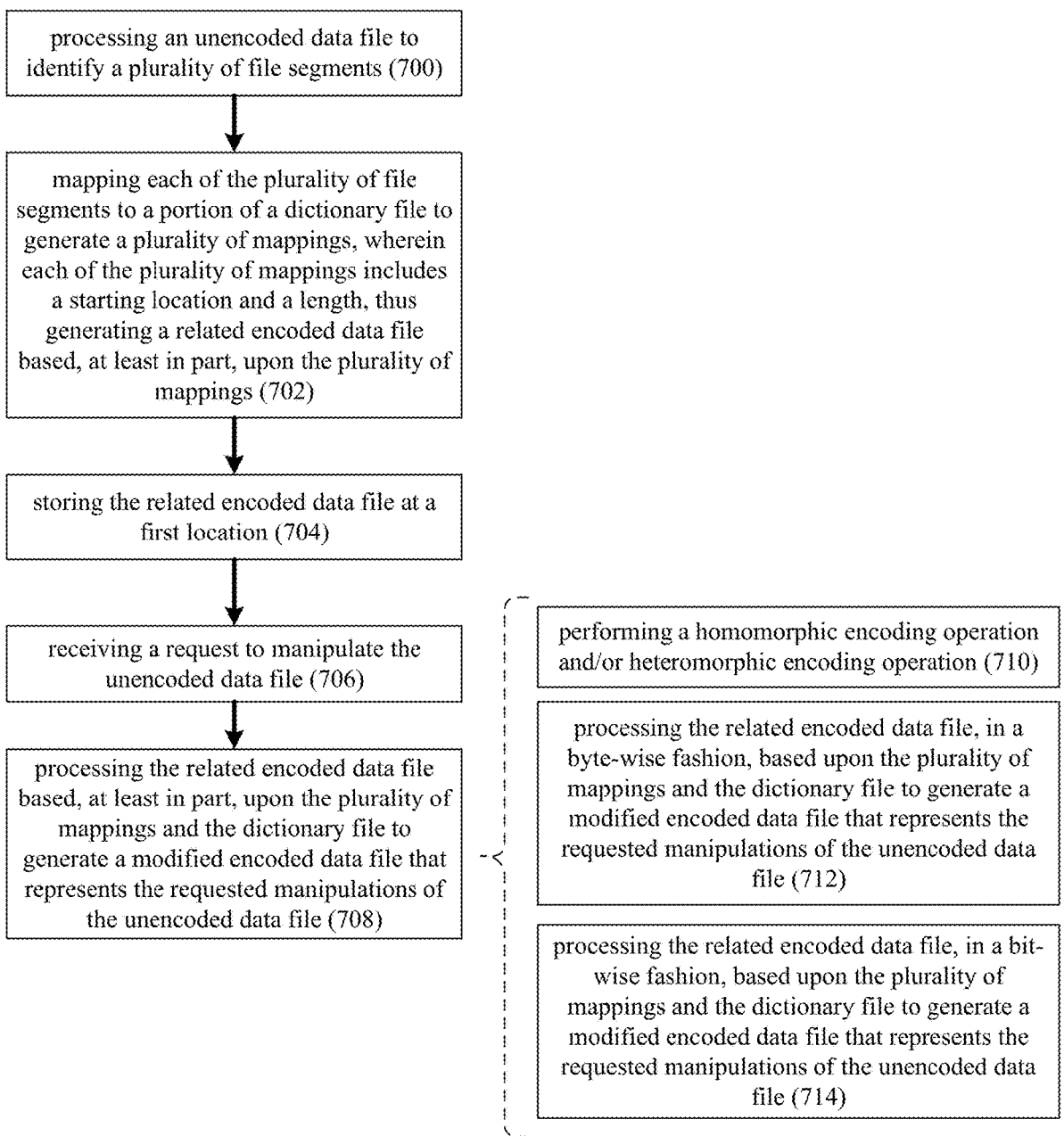
FIG. 13 is a flowchart of the encoding/decoding process of FIG. 1 according to an embodiment of the present disclosure.

The following discussion concerns a use case for encoding/decoding process 10 concerning encoded data at rest. Referring also to FIG. 13, encoding/decoding process 10 may process 700 an unencoded data file (e.g., first data file 100) to identify a plurality of file segments (e.g., plurality of file segments 112).

As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111.

Encoding/decoding process 10 may map 702 each of the plurality of file segments (e.g., plurality of file segments 112) to a portion of a dictionary file (e.g., dictionary file 106) to generate a plurality of mappings (e.g., plurality of mappings 104), wherein each of the plurality of mappings (e.g., plurality of mappings 104) may include a starting location and a length, thus generating a related encoded data file (e.g., related encoded data file 102) based, at least in part, upon the plurality of mappings (e.g., plurality of mappings 104).

As discussed above, one example of such mappings may include but is not limited to:
- a first mapping <28/4> that defines an offset of 28 bits from the beginning of dictionary file 106 and a read length of 4 bits, thus mapping to 0111 within dictionary file 106;
- a second mapping <44/4> that defines an offset of 44 bits from the beginning of dictionary file 106 and a read length of 4 bits, thus mapping to 1011 within dictionary file 106;
- a third mapping <36/4> that defines an offset of 36 bits from the beginning of dictionary file 106 and a read length of 4 bits, thus mapping to 1001 within dictionary file 106; and
- a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>).

Examples of the related encoded data file (e.g., related encoded data file 102) may include but are not limited to a standard (i.e., unstructured) data storage file and a structured data storage file.

As is known in the art, structured data is data that adheres to a pre-defined data model and is, therefore, straightforward to analyze. Structured data conforms to a tabular format with relationship between the different rows and columns. Common examples of structured data are Excel files or SQL databases. Each of these have structured rows and columns that can be sorted. Structured data depends on the existence of a data model—a model of how data can be stored, processed and accessed. Because of a data model, each field is discrete and can be accessed separately or jointly along with data from other fields. This makes structured data extremely powerful: it is possible to quickly aggregate data from various locations in the database.

As in known in the art, unstructured data is information that either does not have a predefined data model or is not organized in a pre-defined manner. Unstructured information is typically text-heavy, but may contain data such as dates, numbers, and facts as well. This results in irregularities and ambiguities that make it difficult to understand using traditional programs as compared to data stored in structured databases. Common examples of unstructured data include audio, video files or No-SQL databases. The ability to store and process unstructured data has greatly grown in recent years, with many new technologies and tools coming to the market that are able to store specialized types of unstructured data. MongoDB, for example, is optimized to store documents. Apache Giraph, as an opposite example, is optimized for storing relationships between nodes.

Encoding/decoding process 10 may store 704 the related encoded data file (e.g., related encoded data file 102) at a first location (e.g., first location 114).

Encoding/decoding process 10 may receive 706 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 706 concerned adding twenty-seven to first data file 100.

Encoding/decoding process 10 may process 708 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 708 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 710 a homomorphic encoding operation; and/or a heteromorphic encoding operation.

When processing 708 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:
- process 712 the related encoded data file (e.g., related encoded data file 102), in a byte-wise fashion to generate modified encoded data file 108 (e.g., in the manner described above); and/or process 714 the related encoded data file (e.g., related encoded data file 102), in a bit-wise fashion to generate modified encoded data file 108 (e.g., in the manner described above).

Encoded Data (at Rest Cloud-Based Storage)

Figure 14:
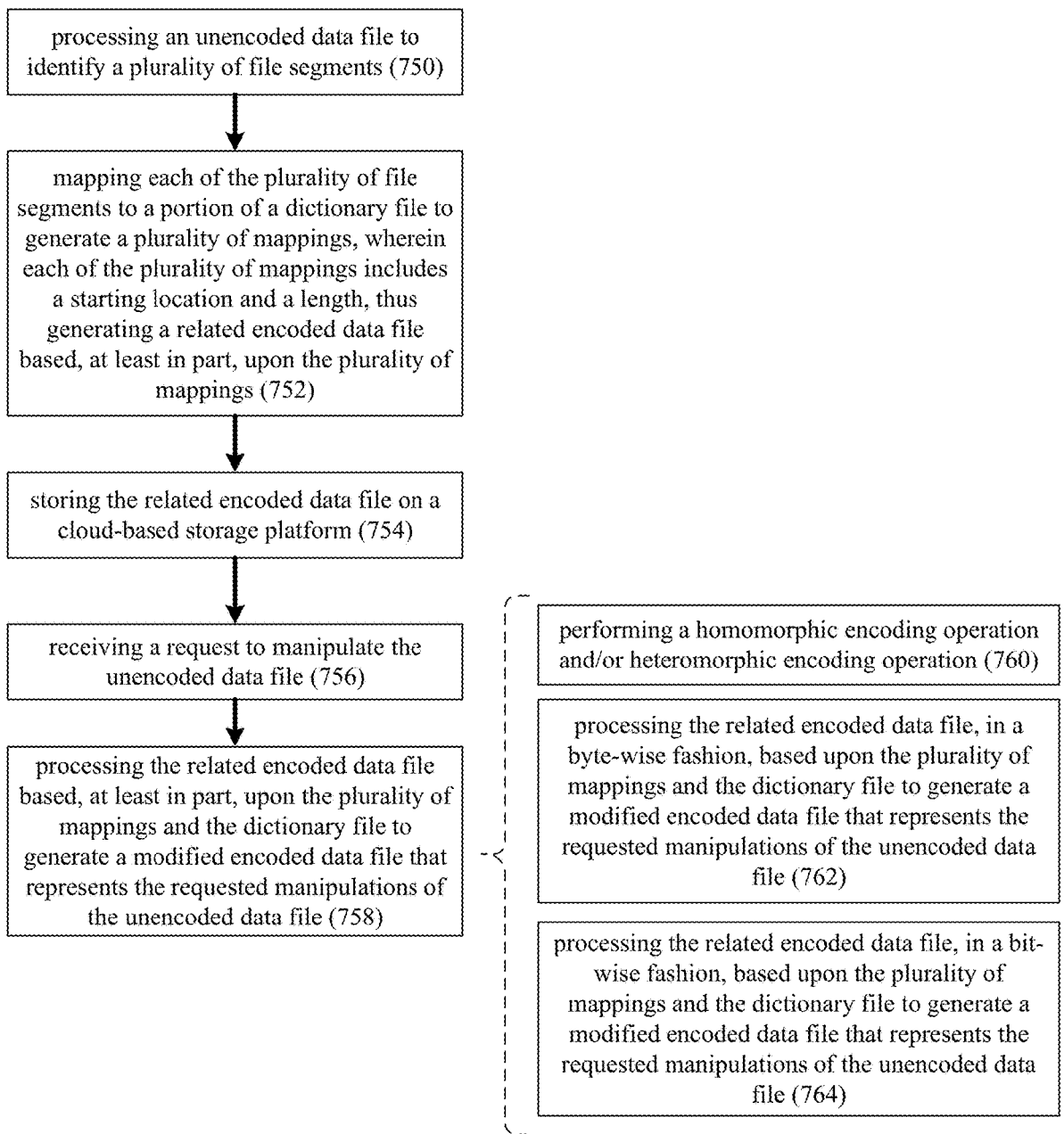
FIG. 14 is a flowchart of the encoding/decoding process of FIG. 1 according to an embodiment of the present disclosure.

The following discussion concerns a use case for encoding/decoding process 10 concerning encoded data at rest in cloud-based storage. Referring also to FIG. 14, encoding/decoding process 10 may process 750 an unencoded data file (e.g., first data file 100) to identify a plurality of file segments (e.g., plurality of file segments 112).

As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111.

Encoding/decoding process 10 may map 752 each of the plurality of file segments (e.g., plurality of file segments 112) to a portion of a dictionary file (e.g., dictionary file 106) to generate a plurality of mappings (e.g., plurality of mappings 104), wherein each of the plurality of mappings (e.g., plurality of mappings 104) may include a starting location and a length, thus generating a related encoded data file (e.g., related encoded data file 102) based, at least in part, upon the plurality of mappings (e.g., plurality of mappings 104).

As discussed above, one example of such mappings may include but is not limited to:
- a first mapping <28/4> that defines an offset of 28 bits from the beginning of dictionary file 106 and a read length of 4 bits, thus mapping to 0111 within dictionary file 106;
- a second mapping <44/4> that defines an offset of 44 bits from the beginning of dictionary file 106 and a read length of 4 bits, thus mapping to 1011 within dictionary file 106;
- a third mapping <36/4> that defines an offset of 36 bits from the beginning of dictionary file 106 and a read length of 4 bits, thus mapping to 1001 within dictionary file 106; and
- a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>).

Encoding/decoding process 10 may store 754 the related encoded data file (e.g., related encoded data file 102) on a cloud-based storage platform (e.g., cloud-based storage platform 126), wherein this related encoded data file (e.g., related encoded data file 102) may be generated on or outside of the cloud-based storage platform (e.g., cloud-based storage platform 126).

As is known in the art, cloud storage is a model of computer data storage in which the digital data is stored in logical pools, said to be on "the cloud". The physical storage spans multiple servers (sometimes in multiple locations), and the physical environment is typically owned and managed by a hosting company. These cloud storage providers are responsible for keeping the data available and accessible, and the physical environment secured, protected, and running. People and organizations buy or lease storage capacity from the providers to store user, organization, or application data. Examples of such providers include Microsoft™, Google™ and Amazon™.

Cloud storage services may be accessed through a co-located cloud computing service, a web service application programming interface (API) or by applications that use the API, such as cloud desktop storage, a cloud storage gateway or Web-based content management systems.

Encoding/decoding process 10 may receive 756 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 756 concerned adding twenty-seven to first data file 100.

Encoding/decoding process 10 may process 758 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 758 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 760 a homomorphic encoding operation; and/or a heteromorphic encoding operation.

When processing 758 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:
- process 762 the related encoded data file (e.g., related encoded data file 102), in a byte-wise fashion to generate modified encoded data file 108 (e.g., in the manner described above); and/or
- process 764 the related encoded data file (e.g., related encoded data file 102), in a bit-wise fashion to generate modified encoded data file 108 (e.g., in the manner described above).

Encoded Data (in Process)

Figure 15:
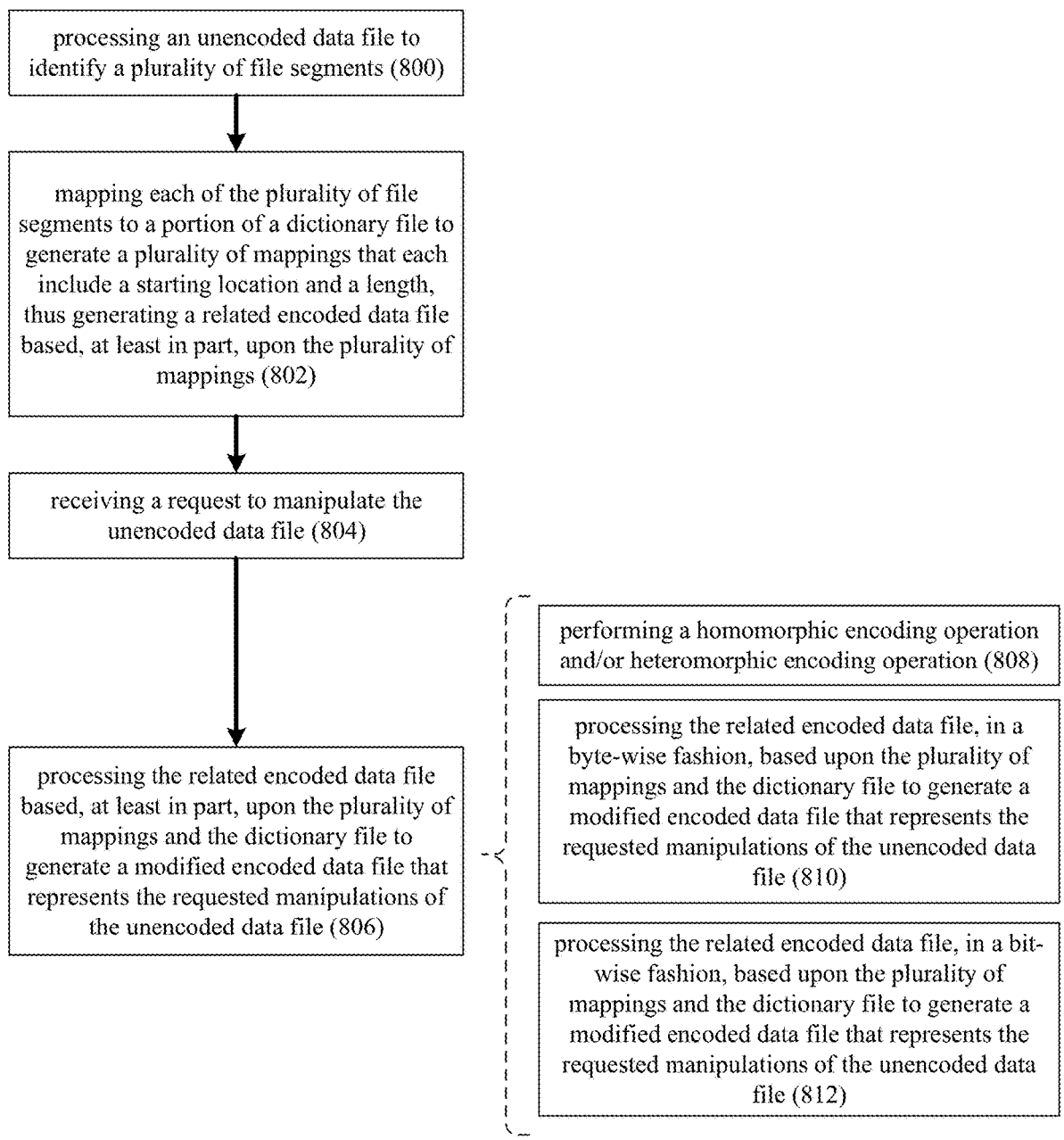
FIG. 15 is a flowchart of the encoding/decoding process of FIG. 1 according to an embodiment of the present disclosure.

The following discussion concerns a use case for encoding/decoding process 10 concerning encoded data in process. Referring also to FIG. 15, encoding/decoding process 10 may process 800 an unencoded data file (e.g., first data file 100) to identify a plurality of file segments (e.g., plurality of file segments 112).

As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111.

Encoding/decoding process 10 may map 802 each of the plurality of file segments (e.g., plurality of file segments 112) to a portion of a dictionary file (e.g., dictionary file 106) to generate a plurality of mappings (e.g., plurality of mappings 104) that each include a starting location and a length, thus generating a related encoded data file (e.g., related encoded data file 102) based, at least in part, upon the plurality of mappings (e.g., plurality of mappings 104).

As discussed above, one example of such mappings may include but is not limited to:
- a first mapping <28/4> that defines an offset of 28 bits from the beginning of dictionary file 106 and a read length of 4 bits, thus mapping to 0111 within dictionary file 106;
- a second mapping <44/4> that defines an offset of 44 bits from the beginning of dictionary file 106 and a read length of 4 bits, thus mapping to 1011 within dictionary file 106;
- a third mapping <36/4> that defines an offset of 36 bits from the beginning of dictionary file 106 and a read length of 4 bits, thus mapping to 1001 within dictionary file 106; and
- a fourth mapping <60/4> that defines an offset of 60 bits from the beginning of dictionary file 106 and a read length of 4 bits, thus mapping to 1111 within dictionary file 106.
- Accordingly and in this example, the related encoded data file (e.g., related encoded data file 102) may include four mappings (e.g., <28/4> <44/4> <36/4> <60/4>).

This related encoded data file (e.g., related encoded data file 102) may be more easily processable and/or require less computational overhead than the unencoded data file (e.g., first data file 100). As discussed above, related encoded data file 102 may be a compressed data file, resulting in related encoded data file 102 being smaller in size than first data file 100. Accordingly, related encoded data file 102 may be more easily processable as the transferring/storing/processing of related encoded data file 102 may require less computational overhead due to this reduced size.

Encoding/decoding process 10 may receive 804 a request (e.g., request 160) to manipulate the unencoded data file (e.g., first data file 100), wherein the requested manipulations may concern one or more of: a computation operation; a search operation; an append operation; a splitting operation; a joining operation; and a concatenating operation. In the example discussed above, the request (e.g., request 160) received 804 concerned adding twenty-seven to first data file 100.

Encoding/decoding process 10 may process 806 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 806 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 808 a homomorphic encoding operation and/or a heteromorphic encoding operation.

When processing 806 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:
- process 810 the related encoded data file (e.g., related encoded data file 102), in a byte-wise fashion to generate modified encoded data file 108 (e.g., in the manner described above); and/or
- process 812 the related encoded data file (e.g., related encoded data file 102), in a bit-wise fashion to generate modified encoded data file 108 (e.g., in the manner described above).

Encoded Data (in Process Machine Learning)

Figure 16:
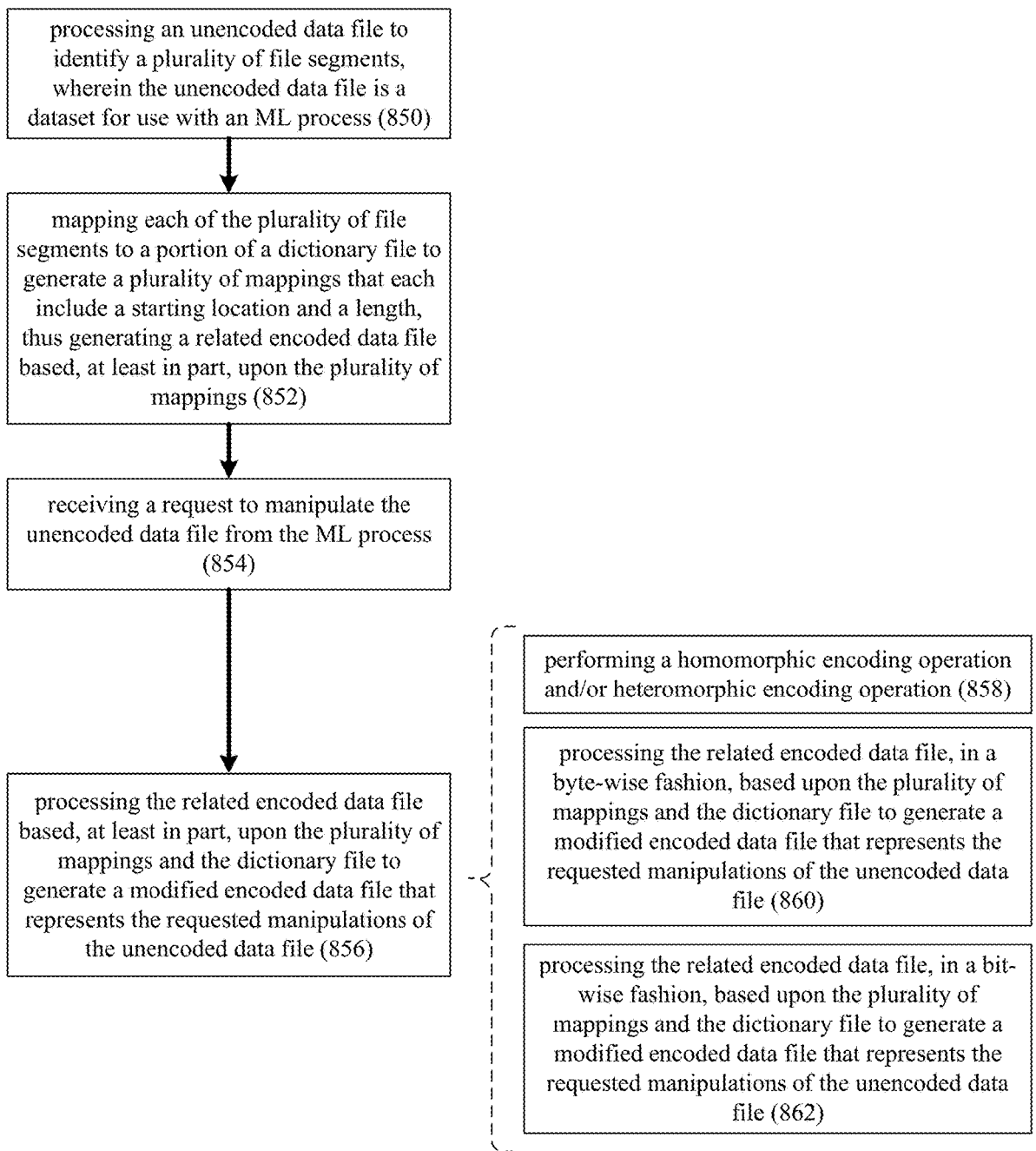
FIG. 16 is a flowchart of the encoding/decoding process of FIG. 1 according to an embodiment of the present disclosure.

The following discussion concerns a use case for encoding/decoding process 10 concerning encoded data in process for machine learning. Referring also to FIG. 16, encoding/decoding process 10 may process 850 an unencoded data file (e.g., first data file 100) to identify a plurality of file segments (e.g., plurality of file segments 112). The unencoded data file (e.g., first data file 100) may be a dataset for use with an ML process (e.g., machine learning process 128).

As discussed in the example above, this first data file (e.g., first data file 100) is:
0111 1011 1001 1111

Accordingly and in this example, plurality of file segments 112 includes four file segments, namely a) 0111, b) 1011, c) 1001 and d) 1111.

As is known in the art, machine learning (ML) is a field of inquiry devoted to understanding and building methods that 'learn', that is, methods that leverage data to improve performance on some set of tasks. It is seen as a part of artificial intelligence. Machine learning algorithms build a model based on sample data, known as training data, in order to make predictions or decisions without being explicitly programmed to do so. Machine learning algorithms are used in a wide variety of applications, such as in medicine, email filtering, speech recognition, and computer vision, where it is difficult or unfeasible to develop conventional algorithms to perform the needed tasks.

A subset of machine learning is closely related to computational statistics, which focuses on making predictions using computers, but not all machine learning is statistical learning. The study of mathematical optimization delivers methods, theory and application domains to the field of machine learning. Data mining is a related field of study, focusing on exploratory data analysis through unsupervised learning. Some implementations of machine learning use data and neural networks in a way that mimics the working of a biological brain. In its application across business problems, machine learning is also referred to as predictive analytics.

As is known in the art, a machine learning system or model may generally include an algorithm or combination of algorithms that has been trained to recognize certain types of patterns. For example, machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As the machine learning system navigates its problem space, the machine learning system is provided feedback that's analogous to rewards, which it tries to maximize. While three examples of machine learning approaches have been provided, it will be appreciated that other machine learning approaches are possible within the scope of the present disclosure.

Encoding/decoding process 10 may map 852 each of the plurality of file segments (e.g., plurality of file segments 112) to a portion of a dictionary file (e.g., dictionary file 106) to generate a plurality of mappings (e.g., plurality of mappings 104) that each include a starting location and a length, thus generating a related encoded data file (e.g., related encoded data file 102) based, at least in part, upon the plurality of mappings (e.g., plurality of mappings 104).

As discussed above, one example of such mappings may include but is not limited to:
 a first mapping <28/4> that defines an offset of 28 bits from the beginning of dictionary file 106 and a read length of 4 bits, thus mapping to 0111 within dictionary file 106;
 a second mapping <44/4> that defines an offset of 44 bits from the beginning of dictionary file 106 and a read length of 4 bits, thus mapping to 1011 within dictionary file 106;
 a third mapping <36/4> that defines an offset of 36 bits from the beginning of dictionary file 106 and a read length of 4 bits, thus mapping to 1001 within dictionary file 106; and
 a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>). One example of this related encoded data file (e.g., related encoded data file 102) may include a massive data set for use with the ML process (e.g., machine learning process 128.

This related encoded data file (e.g., related encoded data file 102) may be more easily processable and/or require less computational overhead than the unencoded data file (e.g., first data file 100). As discussed above, related encoded data file 102 may be a compressed data file, resulting in related encoded data file 102 being smaller in size than first data file 100. Accordingly, related encoded data file 102 may be more easily processable as the transferring/storing/processing of related encoded data file 102 may require less computational overhead due to this reduced size.

Encoding/decoding process 10 may receive 854 a request (e.g., request 160) to manipulate the unencoded data file (e.g., first data file 100) from the ML process (e.g., machine learning process 128), wherein the requested manipulations may concern one or more of: a computation operation; a search operation; an append operation; a splitting operation; a joining operation; and a concatenating operation. In the example discussed above, the request (e.g., request 160) received 854 concerned adding twenty-seven to first data file 100.

Encoding/decoding process 10 may process 856 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 856 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 858 a homomorphic encoding operation and/or a heteromorphic encoding operation.

When processing 856 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:
 process 860 the related encoded data file (e.g., related encoded data file 102), in a byte-wise fashion to generate modified encoded data file 108 (e.g., in the manner described above); and/or
 process 862 the related encoded data file (e.g., related encoded data file 102), in a bit-wise fashion to generate modified encoded data file 108 (e.g., in the manner described above).

Encoded Data (in Process Electronic Health Records)

Figure 17:
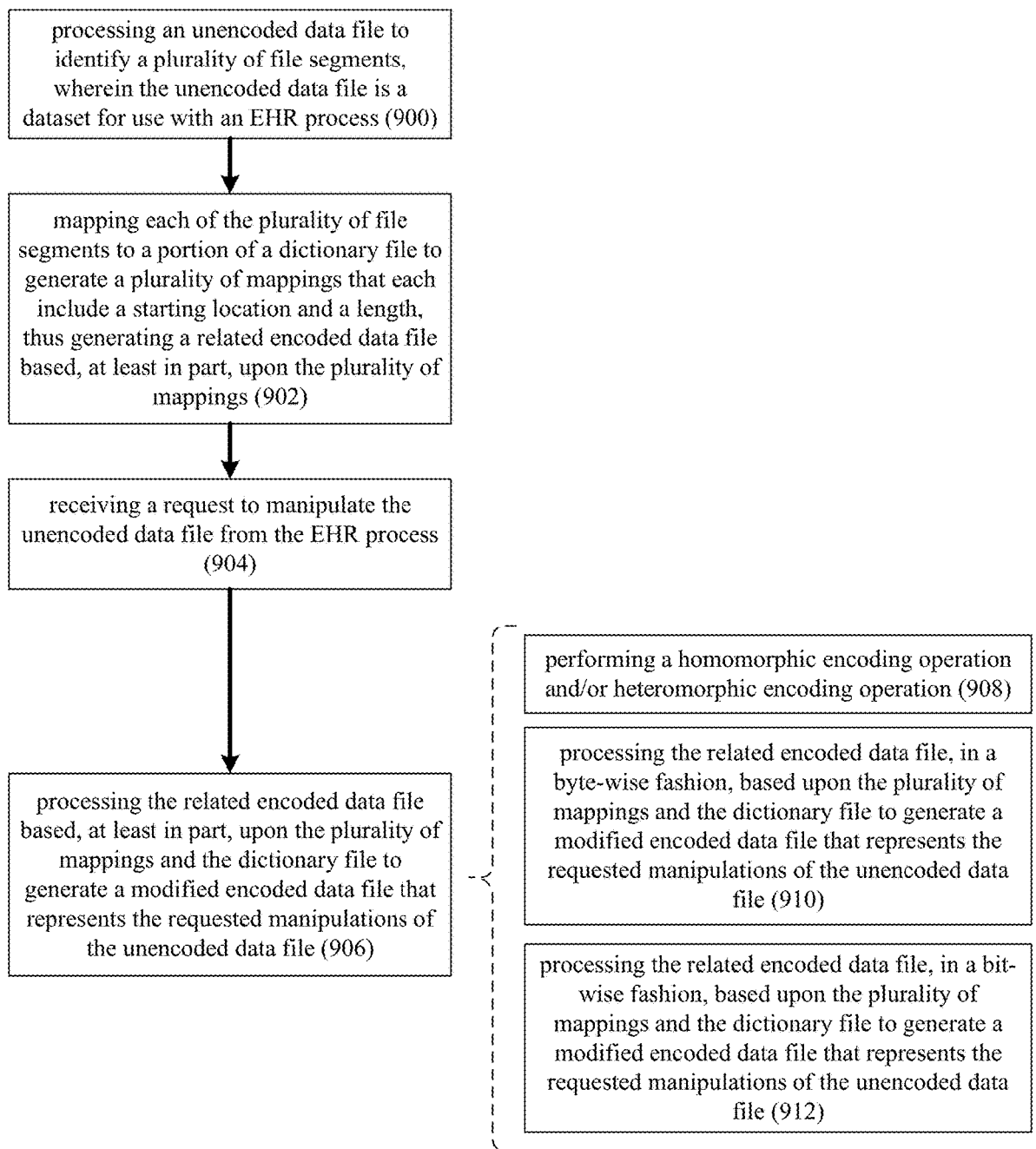
FIG. 17 is a flowchart of the encoding/decoding process of FIG. 1 according to an embodiment of the present disclosure.

The following discussion concerns a use case for encoding/decoding process 10 concerning encoded data in process for electronic health records. Referring also to FIG. 17, encoding/decoding process 10 may process 900 an unencoded data file (e.g., first data file 100) to identify a plurality of file segments (e.g., plurality of file segments 112). The unencoded data file (e.g., first data file 100) may be a dataset for use with an EHR process (e.g., EHR process 130).

As discussed in the example above, this first data file (e.g., first data file 100) is:
0111 1011 1001 1111
Accordingly and in this example, plurality of file segments 112 includes four file segments, namely a) 0111, b) 1011, c) 1001 and d) 1111.

As is known in the art, an electronic health record (EHR) is the systematized collection of patient and population electronically stored health information in a digital format. These records can be shared across different health care settings. Records are shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

Encoding/decoding process 10 may map 902 each of the plurality of file segments (e.g., plurality of file segments 112) to a portion of a dictionary file (e.g., dictionary file 106) to generate a plurality of mappings (e.g., plurality of mappings 104) that each include a starting location and a length, thus generating a related encoded data file (e.g., related encoded data file 102) based, at least in part, upon the plurality of mappings (e.g., plurality of mappings 104).

As discussed above, one example of such mappings may include but is not limited to:
- a first mapping <28/4> that defines an offset of 28 bits from the beginning of dictionary file 106 and a read length of 4 bits, thus mapping to 0111 within dictionary file 106;
- a second mapping <44/4> that defines an offset of 44 bits from the beginning of dictionary file 106 and a read length of 4 bits, thus mapping to 1011 within dictionary file 106;
- a third mapping <36/4> that defines an offset of 36 bits from the beginning of dictionary file 106 and a read length of 4 bits, thus mapping to 1001 within dictionary file 106; and
- a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>). One example of this related encoded data file (e.g., related encoded data file 102) may include medical health records for use with the EHR process (e.g., EHR process 130).

This related encoded data file (e.g., related encoded data file 102) may be more easily processable and/or require less computational overhead than the unencoded data file (e.g., first data file 100). As discussed above, related encoded data file 102 may be a compressed data file, resulting in related encoded data file 102 being smaller in size than first data file 100. Accordingly, related encoded data file 102 may be more easily processable as the transferring/storing/processing of related encoded data file 102 may require less computational overhead due to this reduced size.

Encoding/decoding process 10 may receive 904 a request (e.g., request 160) to manipulate the unencoded data file (e.g., first data file 100) from the EHR process (e.g., EHR process 130), wherein the requested manipulations may concern one or more of: a computation operation; a search operation; an append operation; a splitting operation; a joining operation; and a concatenating operation. In the example discussed above, the request (e.g., request 160) received 904 concerned adding twenty-seven to first data file 100.

Encoding/decoding process 10 may process 906 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 906 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 908 a homomorphic encoding operation and/or a heteromorphic encoding operation.

When processing 906 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:
- process 910 the related encoded data file (e.g., related encoded data file 102), in a byte-wise fashion to generate modified encoded data file 108 (e.g., in the manner described above); and/or
- process 912 the related encoded data file (e.g., related encoded data file 102), in a bit-wise fashion to generate modified encoded data file 108 (e.g., in the manner described above).

Encoded Data (in Process Blockchain)

Figure 18:
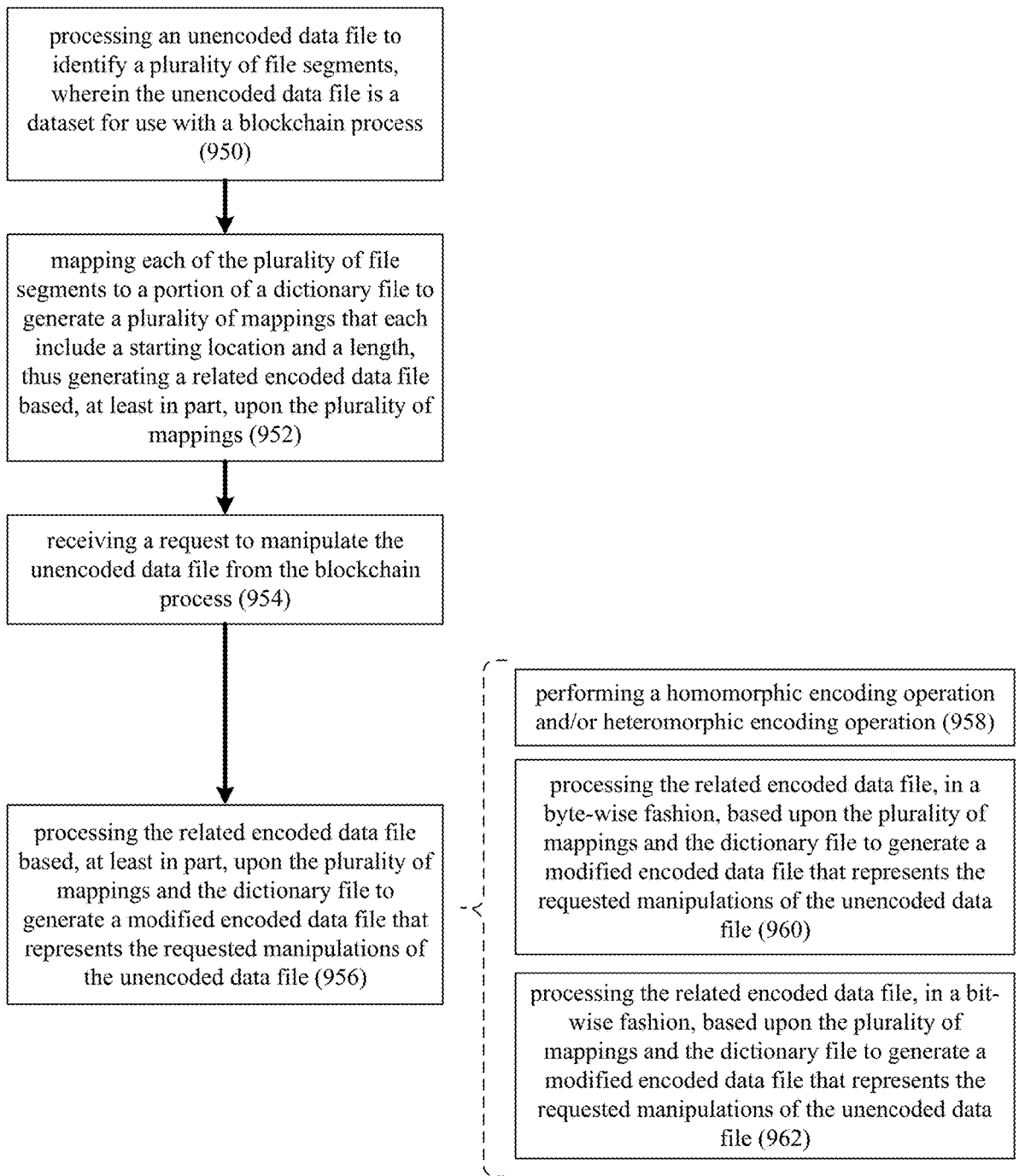
FIG. 18 is a flowchart of the encoding/decoding process of FIG. 1 according to an embodiment of the present disclosure.

The following discussion concerns a use case for encoding/decoding process 10 concerning encoded data in process for blockchain. Referring also to FIG. 18, encoding/decoding process 10 may process 950 an unencoded data file (e.g., first data file 100) to identify a plurality of file segments (e.g., plurality of file segments 112). The unencoded data file (e.g., first data file 100) may be a dataset for use with a blockchain process (e.g., blockchain process 132).

As discussed in the example above, this first data file (e.g., first data file 100) is:
0111 1011 1001 1111

Accordingly and in this example, plurality of file segments 112 includes four file segments, namely a) 0111, b) 1011, c) 1001 and d) 1111.

As is known in the art, a blockchain is a type of distributed ledger technology (DLT) that consists of growing list of records, called blocks, that are securely linked together using cryptography. Each block contains a cryptographic hash of the previous block, a timestamp, and transaction data (generally represented as a Merkle tree, where data nodes are represented by leaves). The timestamp proves that the transaction data existed when the block was created. Since each block contains information about the block previous to it, they effectively form a chain (compare linked list data structure), with each additional block linking to the ones before it. Consequently, blockchain transactions are irreversible in that, once they are recorded, the data in any given block cannot be altered retroactively without altering all subsequent blocks.

Encoding/decoding process 10 may map 952 each of the plurality of file segments (e.g., plurality of file segments 112) to a portion of a dictionary file (e.g., dictionary file 106) to generate a plurality of mappings (e.g., plurality of mappings 104) that each include a starting location and a length, thus generating a related encoded data file (e.g., related encoded data file 102) based, at least in part, upon the plurality of mappings (e.g., plurality of mappings 104).

As discussed above, one example of such mappings may include but is not limited to:
- a first mapping <28/4> that defines an offset of 28 bits from the beginning of dictionary file 106 and a read length of 4 bits, thus mapping to 0111 within dictionary file 106;
- a second mapping <44/4> that defines an offset of 44 bits from the beginning of dictionary file 106 and a read length of 4 bits, thus mapping to 1011 within dictionary file 106;
- a third mapping <36/4> that defines an offset of 36 bits from the beginning of dictionary file 106 and a read length of 4 bits, thus mapping to 1001 within dictionary file 106; and
- a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>). One example of the related encoded data file (e.g., related encoded data file 102) may include a distributed ledger for use with the blockchain process (e.g., blockchain process 132)

This related encoded data file (e.g., related encoded data file 102) may be more easily processable and/or require less computational overhead than the unencoded data file (e.g., first data file 100). As discussed above, related encoded data file 102 may be a compressed data file, resulting in related encoded data file 102 being smaller in size than first data file 100. Accordingly, related encoded data file 102 may be more easily processable as the transferring/storing/processing of related encoded data file 102 may require less computational overhead due to this reduced size.

Encoding/decoding process 10 may receive 954 a request (e.g., request 160) to manipulate the unencoded data file (e.g., first data file 100) from the blockchain process (e.g., blockchain process 132), wherein the requested manipulations may concern one or more of: a computation operation; a search operation; an append operation; a splitting operation; a joining operation; and a concatenating operation. In the example discussed above, the request (e.g., request 160) received 954 concerned adding twenty-seven to first data file 100.

Encoding/decoding process 10 may process 956 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 956 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 958 a homomorphic encoding operation and/or a heteromorphic encoding operation.

When processing 956 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:
- process 960 the related encoded data file (e.g., related encoded data file 102), in a byte-wise fashion to generate modified encoded data file 108 (e.g., in the manner described above); and/or
- process 962 the related encoded data file (e.g., related encoded data file 102), in a bit-wise fashion to generate modified encoded data file 108 (e.g., in the manner described above).

Encoded Data (in Process Disaster Recovery)

Figure 19:
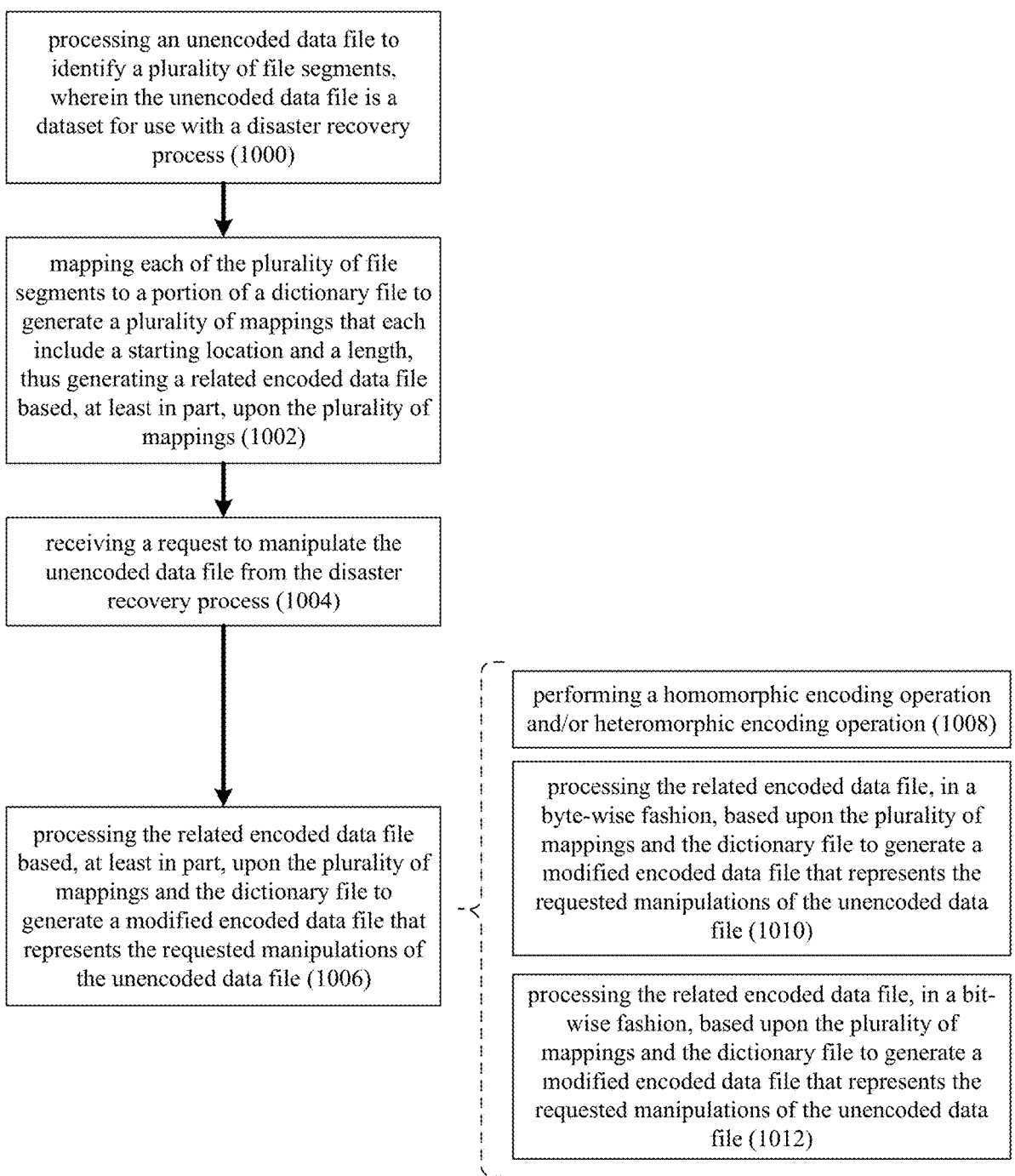
FIG. 19 is a flowchart of the encoding/decoding process of FIG. 1 according to an embodiment of the present disclosure.

The following discussion concerns a use case for encoding/decoding process 10 concerning encoded data in process for disaster recovery. Referring also to FIG. 19, encoding/decoding process 10 may process 1000 an unencoded data file (e.g., first data file 100) to identify a plurality of file segments (e.g., plurality of file segments 112). The unencoded data file (e.g., first data file 100) may be a dataset for use with a disaster recovery process (e.g., disaster recovery process 134).

As discussed in the example above, this first data file (e.g., first data file 100) is:

0111 1011 1001 1111

Accordingly and in this example, plurality of file segments 112 includes four file segments, namely a) 0111, b) 1011, c) 1001 and d) 1111.

Disaster recovery involves a set of policies, tools, and procedures to enable the recovery or continuation of vital technology infrastructure and systems following a natural or human-induced disaster. Disaster recovery focuses on the information technology (IT) or technology systems supporting critical business functions as opposed to business continuity. This involves keeping all essential aspects of a business functioning despite significant disruptive events; it can therefore be considered a subset of business continuity. Disaster recovery assumes that the primary site is not recoverable for some time and represents a process of restoring data and services to a secondary survived site, which is opposite to restoring it back to its original place.

Encoding/decoding process 10 may map 1002 each of the plurality of file segments (e.g., plurality of file segments 112) to a portion of a dictionary file (e.g., dictionary file 106) to generate a plurality of mappings (e.g., plurality of mappings 104) that each include a starting location and a length, thus generating a related encoded data file (e.g., related encoded data file 102) based, at least in part, upon the plurality of mappings (e.g., plurality of mappings 104).

As discussed above, one example of such mappings may include but is not limited to:
- a first mapping <28/4> that defines an offset of 28 bits from the beginning of dictionary file 106 and a read length of 4 bits, thus mapping to 0111 within dictionary file 106;

a second mapping <44/4> that defines an offset of 44 bits from the beginning of dictionary file 106 and a read length of 4 bits, thus mapping to 1011 within dictionary file 106;

a third mapping <36/4> that defines an offset of 36 bits from the beginning of dictionary file 106 and a read length of 4 bits, thus mapping to 1001 within dictionary file 106; and a fourth mapping <60/4> that defines an offset of 60 bits from the beginning of dictionary file 106 and a read length of 4 bits, thus mapping to 1111 within dictionary file 106.

Accordingly and in this example, the related encoded data file (e.g., related encoded data file 102) may include four mappings (e.g., <28/4> <44/4> <36/4> <60/4>). One example of the related encoded data file (e.g., related encoded data file 102) may include a recovery data set for use with the disaster recovery process (e.g., disaster recovery process 134).

This related encoded data file (e.g., related encoded data file 102) may be more easily processable and/or require less computational overhead than the unencoded data file (e.g., first data file 100). As discussed above, related encoded data file 102 may be a compressed data file, resulting in related encoded data file 102 being smaller in size than first data file 100. Accordingly, related encoded data file 102 may be more easily processable as the transferring/storing/processing of related encoded data file 102 may require less computational overhead due to this reduced size.

Encoding/decoding process 10 may receive 1004 a request (e.g., request 160) to manipulate the unencoded data file (e.g., first data file 100) from the disaster recovery process (e.g., disaster recovery process 134), wherein the requested manipulations may concern one or more of: a computation operation; a search operation; an append operation; a splitting operation; a joining operation; and a concatenating operation. In the example discussed above, the request (e.g., request 160) received 1004 concerned adding twenty-seven to first data file 100.

Encoding/decoding process 10 may process 1006 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100). In the example discussed above, encoding/decoding process 10 utilized plurality of mappings 104 and dictionary file 106 to generate result 110, which was subsequently encoded to generate modified encoded data file 108.

As discussed above, when processing 1006 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may: perform 1008 a homomorphic encoding operation and/or a heteromorphic encoding operation.

When processing 1006 the related encoded data file (e.g., related encoded data file 102) based, at least in part, upon the plurality of mappings (e.g., plurality of mappings 104) and the dictionary file (e.g., dictionary file 106) to generate a modified encoded data file (e.g., modified encoded data file 108) that represents the requested manipulations of the unencoded data file (e.g., first data file 100), encoding/decoding process 10 may:

process 1010 the related encoded data file (e.g., related encoded data file 102), in a byte-wise fashion to generate modified encoded data file 108 (e.g., in the manner described above); and/or process 1012 the related encoded data file (e.g., related encoded data file 102), in a bit-wise fashion to generate modified encoded data file 108 (e.g., in the manner described above).

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a standalone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device comprising:

processing an unencoded data file to identify a plurality of file segments;

mapping each of the plurality of file segments to a portion of a dictionary file to generate a plurality of mappings that each include a starting location as an offset within the dictionary file and a length as a number of bits within the dictionary file beginning from the starting location, thus generating a related encoded data file based, at least in part, upon the plurality of mappings, wherein mapping each of the plurality of file segments to the portion of the dictionary file to generate the plurality of mappings includes mapping each of the plurality of file segments to a plurality of bits within the dictionary file using the starting location and length, wherein the dictionary file includes a binary sequence of all possible combinations of a predefined number having a defined bit length;

receiving a request to manipulate the unencoded data file; and processing the related encoded data file based, at least in part, upon the plurality of mappings and the dictionary file to generate a modified encoded data file that represents the requested manipulations of the unencoded data file, wherein processing the related encoded data file based, at least in part, upon the plurality of mappings and the dictionary file to generate a modified encoded data file that represents the requested manipulations of the unencoded data file includes one or more of: performing a homomorphic encoding operation; and performing a heteromorphic encoding operation; and storing the related encoded data file on a cloud-based storage platform.

2. The computer-implemented method of claim 1 wherein the related encoded data file includes one or more of:

a related compressed data file; and a related encrypted data file.

3. The computer-implemented method of claim 1 wherein the dictionary file includes a plurality of discrete entries.

4. The computer-implemented method of claim 3 wherein processing the related encoded data file based, at least in part, upon the plurality of mappings and the dictionary file to generate a modified encoded data file that represents the requested manipulations of the unencoded data file includes:
processing the related encoded data file, in a byte-wise fashion, based upon the plurality of mappings and the dictionary file to generate a modified encoded data file that represents the requested manipulations of the unencoded data file.

5. The computer-implemented method of claim 1 wherein the dictionary file includes a plurality of concatenated entries.

6. The computer-implemented method of claim 5 wherein processing the related encoded data file based, at least in part, upon the plurality of mappings and the dictionary file to generate a modified encoded data file that represents the requested manipulations of the unencoded data file includes:
processing the related encoded data file, in a bit-wise fashion, based upon the plurality of mappings and the dictionary file to generate a modified encoded data file that represents the requested manipulations of the unencoded data file.

7. The computer-implemented method of claim 1 wherein the related encoded data file is generated on the cloud-based storage platform.

8. The computer-implemented method of claim 1 wherein the related encoded data file is generated outside of the cloud-based storage platform.

9. A computer program product residing on a non-transitory computer readable medium having a plurality of instructions stored thereon which, when executed by a processor, cause the processor to perform operations comprising:
processing an unencoded data file to identify a plurality of file segments;
mapping each of the plurality of file segments to a portion of a dictionary file to generate a plurality of mappings that each include a starting location as a bit-wise offset within the dictionary file and a length as a number of bits within the dictionary file beginning from the starting location, thus generating a related encoded data file based, at least in part, upon the plurality of mappings, wherein mapping each of the plurality of file segments to the portion of the dictionary file to generate the plurality of mappings includes mapping each of the plurality of file segments to a plurality of bits within the dictionary file using the starting location and length, wherein the dictionary file includes a binary sequence of all possible combinations of a predefined number having a defined bit length;
receiving a request to manipulate the unencoded data file; and
processing the related encoded data file based, at least in part, upon the plurality of mappings and the dictionary file to generate a modified encoded data file that represents the requested manipulations of the unencoded data file, wherein processing the related encoded data file based, at least in part, upon the plurality of mappings and the dictionary file to generate a modified encoded data file that represents the requested manipulations of the unencoded data file includes one or more of: performing a homomorphic encoding operation; and performing a heteromorphic encoding operation; and
storing the related encoded data file on a cloud-based storage platform.

10. The computer-implemented method of claim 9 wherein the related encoded data file includes one or more of:
a related compressed data file; and
a related encrypted data file.

11. The computer-implemented method of claim 9 wherein the dictionary file includes a plurality of discrete entries.

12. The computer-implemented method of claim 11 wherein processing the related encoded data file based, at least in part, upon the plurality of mappings and the dictionary file to generate a modified encoded data file that represents the requested manipulations of the unencoded data file includes:
processing the related encoded data file, in a byte-wise fashion, based upon the plurality of mappings and the dictionary file to generate a modified encoded data file that represents the requested manipulations of the unencoded data file.

13. The computer-implemented method of claim 9 wherein the dictionary file includes a plurality of concatenated entries.

14. The computer-implemented method of claim 13 wherein processing the related encoded data file based, at least in part, upon the plurality of mappings and the dictionary file to generate a modified encoded data file that represents the requested manipulations of the unencoded data file includes:
processing the related encoded data file, in a bit-wise fashion, based upon the plurality of mappings and the dictionary file to generate a modified encoded data file that represents the requested manipulations of the unencoded data file.

15. The computer-implemented method of claim 9 wherein the related encoded data file is generated on the cloud-based storage platform.

16. The computer-implemented method of claim 9 wherein the related encoded data file is generated outside of the cloud-based storage platform.

17. A computing system including a processor and memory configured to perform operations comprising:
processing an unencoded data file to identify a plurality of file segments;
mapping each of the plurality of file segments to a portion of a dictionary file to generate a plurality of mappings that each include a starting location as a bit-wise offset within the dictionary file and a length as a number of bits within the dictionary file beginning from the starting location, thus generating a related encoded data file based, at least in part, upon the plurality of mappings, wherein mapping each of the plurality of file segments to the portion of the dictionary file to generate the plurality of mappings includes mapping each of the plurality of file segments to a plurality of bits within the dictionary file using the starting location and length, wherein the dictionary file includes a binary sequence of all possible combinations of a predefined number having a defined bit length;
receiving a request to manipulate the unencoded data file; and
processing the related encoded data file based, at least in part, upon the plurality of mappings and the dictionary file to generate a modified encoded data file that represents the requested manipulations of the unencoded data file, wherein processing the related encoded data file based, at least in part, upon the plurality of mappings and the dictionary file to generate a modified encoded data file that represents the requested manipulations of the unencoded data file includes one or more of: performing a homomorphic encoding operation; and performing a heteromorphic encoding operation; and storing the related encoded data file on a cloud-based storage platform.

18. The computer-implemented method of claim 17 wherein the related encoded data file includes one or more of:
a related compressed data file; and
a related encrypted data file.

19. The computer-implemented method of claim 17 wherein the dictionary file includes a plurality of discrete entries.

20. The computer-implemented method of claim 19 wherein processing the related encoded data file based, at least in part, upon the plurality of mappings and the dictionary file to generate a modified encoded data file that represents the requested manipulations of the unencoded data file includes:
processing the related encoded data file, in a byte-wise fashion, based upon the plurality of mappings and the dictionary file to generate a modified encoded data file that represents the requested manipulations of the unencoded data file.

21. The computer-implemented method of claim 17 wherein the dictionary file includes a plurality of concatenated entries.

22. The computer-implemented method of claim 21 wherein processing the related encoded data file based, at least in part, upon the plurality of mappings and the dictionary file to generate a modified encoded data file that represents the requested manipulations of the unencoded data file includes:
processing the related encoded data file, in a bit-wise fashion, based upon the plurality of mappings and the dictionary file to generate a modified encoded data file that represents the requested manipulations of the unencoded data file.

23. The computer-implemented method of claim 17 wherein the related encoded data file is generated on the cloud-based storage platform.

24. The computer-implemented method of claim 17 wherein the related encoded data file is generated outside of the cloud-based storage platform.

* * * * *